US010603421B2

(12) United States Patent
Merchant

(10) Patent No.: US 10,603,421 B2
(45) Date of Patent: Mar. 31, 2020

(54) CARTRIDGES USEFUL IN CLEANING DIALYSIS SOLUTIONS

(71) Applicant: Fresenius Medical Care Holdings, Inc., Waltham, MA (US)

(72) Inventor: Stephen A. Merchant, Oklahoma City, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 174 days.

(21) Appl. No.: 15/736,784

(22) PCT Filed: Jul. 22, 2016

(86) PCT No.: PCT/US2016/043442
§ 371 (c)(1),
(2) Date: Dec. 15, 2017

(87) PCT Pub. No.: WO2017/048358
PCT Pub. Date: Mar. 23, 2017

(65) Prior Publication Data
US 2018/0177933 A1    Jun. 28, 2018

Related U.S. Application Data

(60) Provisional application No. 62/219,369, filed on Sep. 16, 2015.

(51) Int. Cl.
*A61M 1/16* (2006.01)
*B01D 15/22* (2006.01)
(Continued)

(52) U.S. Cl.
CPC ............ *A61M 1/1696* (2013.01); *A61M 1/28* (2013.01); *B01D 15/206* (2013.01); *B01D 15/22* (2013.01);
(Continued)

(58) Field of Classification Search
CPC .................. A61M 1/1696; A61M 1/28; A61M 2205/3331; A61M 2207/00;
(Continued)

(56) References Cited

U.S. PATENT DOCUMENTS 3,669,878 A    6/1972 Marantz et al.
3,669,880 A    6/1972 Marantz et al.
(Continued)

FOREIGN PATENT DOCUMENTS

EP    2168681 A2    3/2010
WO    03045472 A1    6/2003
(Continued)

OTHER PUBLICATIONS

International Search Report and Written Opinion issued in corresponding International Patent Application No. PCT/US2016/043442 dated Oct. 14, 2016 (11 pages).
(Continued)

*Primary Examiner* — Matthew O Savage
(74) *Attorney, Agent, or Firm* — Kilyk & Bowersox, P.L.L.C.

(57) ABSTRACT

Cartridges useful in regenerating or purifying dialysis solutions are described as well as methods to regenerate or purify spent dialysis solutions. Dialysis methods using the sorbent cartridges of the present invention are further described.

23 Claims, 11 Drawing Sheets

(51) Int. Cl.

| | | |
|---|---|---|
| B01J 47/022 | (2017.01) | |
| B01J 20/20 | (2006.01) | |
| B01J 20/28 | (2006.01) | |
| B01J 20/02 | (2006.01) | |
| B01J 20/06 | (2006.01) | |
| B01J 47/024 | (2017.01) | |
| B01D 15/20 | (2006.01) | |
| B01J 39/09 | (2017.01) | |
| A61M 1/28 | (2006.01) | |
| B01J 20/30 | (2006.01) | |
| B01J 39/02 | (2006.01) | |
| B01J 41/02 | (2006.01) | |
| B01J 41/10 | (2006.01) | |

(52) U.S. Cl.
CPC ....... *B01J 20/0211* (2013.01); *B01J 20/0292* (2013.01); *B01J 20/06* (2013.01); *B01J 20/20* (2013.01); *B01J 20/28004* (2013.01); *B01J 20/28011* (2013.01); *B01J 20/28052* (2013.01); *B01J 20/3092* (2013.01); *B01J 39/02* (2013.01); *B01J 39/09* (2017.01); *B01J 41/02* (2013.01); *B01J 41/10* (2013.01); *B01J 47/024* (2013.01); *A61M 2205/127* (2013.01); *A61M 2205/15* (2013.01); *A61M 2205/3317* (2013.01); *A61M 2205/3331* (2013.01); *A61M 2205/3334* (2013.01); *A61M 2205/3368* (2013.01); *A61M 2207/00* (2013.01); *B01J 2220/62* (2013.01)

(58) Field of Classification Search
CPC .. A61M 2205/3368; A61M 2205/3334; A61M 2205/3317; A61M 2205/15; A61M 2205/127; B01J 20/0292; B01J 20/06; B01J 20/0211; B01J 41/10; B01J 41/02; B01J 39/02; B01J 20/3092; B01J 20/28011; B01J 20/28004; B01J 39/09; B01J 20/28052; B01J 20/20; B01J 2220/62; B01J 47/022; B01J 47/024; B01J 47/026; B01D 15/22; B01D 15/206; B01D 15/08; B01D 24/001; B01D 24/002; B01D 24/004

See application file for complete search history.

(56) References Cited

U.S. PATENT DOCUMENTS

| | | | |
|---|---|---|---|
| 3,697,410 | A | 10/1972 | Johnson et al. |
| 3,697,418 | A | 10/1972 | Johnson |
| 3,703,959 | A | 11/1972 | Raymond |
| 3,850,835 | A | 11/1974 | Marantz et al. |
| 3,989,622 | A | 11/1976 | Marantz et al. |
| 3,989,625 | A | 11/1976 | Mason |
| 4,025,608 | A | 5/1977 | Tawil et al. |
| 4,213,859 | A | 7/1980 | Smakman et al. |
| 4,256,718 | A | 3/1981 | McArthur et al. |
| 4,360,507 | A | 11/1982 | McArthur et al. |
| 4,460,555 | A | 7/1984 | Thompson |
| 4,484,599 | A | 11/1984 | Hanover et al. |
| 4,495,129 | A | 1/1985 | Newberry et al. |
| 4,558,996 | A | 12/1985 | Becker |
| 4,560,472 | A | 12/1985 | Granzow et al. |
| D282,578 | S | 2/1986 | Humphreys et al. |
| 4,738,668 | A | 4/1988 | Bellotti et al. |
| 5,326,036 | A | 7/1994 | Wilger |
| 5,498,338 | A | 3/1996 | Kruger et al. |
| 5,597,805 | A | 1/1997 | Breborowicz et al. |
| 5,631,025 | A | 5/1997 | Shockley et al. |
| 5,641,405 | A | 6/1997 | Keshaviah et al. |
| 5,704,915 | A | 1/1998 | Melsky et al. |
| 5,782,796 | A | 7/1998 | Din et al. |
| 5,824,213 | A | 10/1998 | Utterberg |
| 5,938,634 | A | 8/1999 | Packard |
| 5,955,450 | A | 9/1999 | Breborowicz et al. |
| 5,968,966 | A | 10/1999 | Bergstrom |
| 5,980,481 | A | 11/1999 | Gorsuch |
| 5,984,891 | A | 11/1999 | Keilman et al. |
| 6,017,942 | A | 1/2000 | Bergstrom |
| 6,074,359 | A | 6/2000 | Keshaviah et al. |
| 6,117,122 | A | 9/2000 | Din et al. |
| 6,146,536 | A | 11/2000 | Twardowski |
| 6,196,992 | B1 | 3/2001 | Keilman et al. |
| 6,274,103 | B1 | 8/2001 | Taylor |
| 6,284,131 | B1 | 9/2001 | Hogard et al. |
| 6,284,139 | B1 | 9/2001 | Piccirillo |
| 6,293,921 | B1 | 9/2001 | Shinmoto et al. |
| 6,299,769 | B1 | 10/2001 | Falkvall et al. |
| 6,306,836 | B1 | 10/2001 | Martis et al. |
| 6,309,673 | B1 | 10/2001 | Duponchelle et al. |
| 6,627,164 | B1 | 9/2003 | Wong |
| 6,878,283 | B2 | 4/2005 | Thompson |
| 7,033,498 | B2 | 4/2006 | Wong |
| 7,241,272 | B2 | 7/2007 | Karoor et al. |
| 8,012,118 | B2 | 9/2011 | Curtin et al. |
| 8,343,346 | B2 | 1/2013 | Crnkovich et al. |
| 8,366,921 | B2 | 2/2013 | Beden et al. |
| 8,475,399 | B2 | 7/2013 | Fulkerson |
| 8,500,994 | B2 | 8/2013 | Weaver et al. |
| 8,580,112 | B2 | 11/2013 | Updyke et al. |
| 8,597,505 | B2 | 12/2013 | Fulkerson et al. |
| 8,663,463 | B2 | 3/2014 | Weaver et al. |
| 9,707,330 | B2 | 7/2017 | Kelly et al. |
| 9,962,477 | B2 * | 5/2018 | Slade ............... A61M 1/1696 |
| 2002/0112609 | A1 | 8/2002 | Wong |
| 2003/0098270 | A1 * | 5/2003 | Thompson ......... A61M 1/1696 |
| | | | 210/283 |
| 2005/0045232 | A1 | 3/2005 | Van Decker |
| 2005/0230302 | A1 * | 10/2005 | Muir ................. B01D 24/008 |
| | | | 210/290 |
| 2006/0140840 | A1 | 6/2006 | Wong |
| 2010/0078387 | A1 | 4/2010 | Wong |
| 2010/0217181 | A1 | 8/2010 | Roberts et al. |
| 2011/0203985 | A1 | 8/2011 | Reid |
| 2012/0234762 | A1 | 9/2012 | Wong |
| 2013/0030356 | A1 | 1/2013 | Ding et al. |
| 2013/0190168 | A1 | 7/2013 | Wong et al. |
| 2013/0199998 | A1 | 8/2013 | Kelly et al. |
| 2013/0206706 | A1 | 8/2013 | Ekholm et al. |
| 2014/0231302 | A1 | 8/2014 | Goyal |
| 2014/0326671 | A1 | 11/2014 | Kelly et al. |
| 2015/0144542 | A1 | 5/2015 | Pudil et al. |
| 2015/0258266 | A1 | 9/2015 | Merchant et al. |
| 2017/0189598 | A1 | 7/2017 | Slade |

FOREIGN PATENT DOCUMENTS

| | | |
|---|---|---|
| WO | 2009157877 A1 | 12/2009 |
| WO | 2012057941 A2 | 5/2012 |
| WO | 2013/028809 A2 | 2/2013 |
| WO | 2015/080895 A1 | 6/2015 |

OTHER PUBLICATIONS

Cobe Renal Care, Inc., "Guide to Custom Dialysis," Product No. 306100-005, Revision E, Sep. 1993, pp. 1-52 (54 pages).

Cobe Renal Care, Inc., "Sorbent Dialysis Primer," Product No. 306100-006, Edition 4, Sep. 1993, pp. 1-46 (56 pages).

Ash, "Sorbent Dialysis Systems: An Expert Commentary by Stephen R. Ash, MD, FACP," http://www.medscape.com/viewarticle/576534_print, Aug. 5, 2008 (11 pages).

Sung et al., "A Procedure for Purifying Jack Bean Urease for Clinical Use," Database Biosis (Online), Biosciences Information Service, Philadelphia, Pennsylvania, US, 1989, (1 page) (Abstract).

* cited by examiner

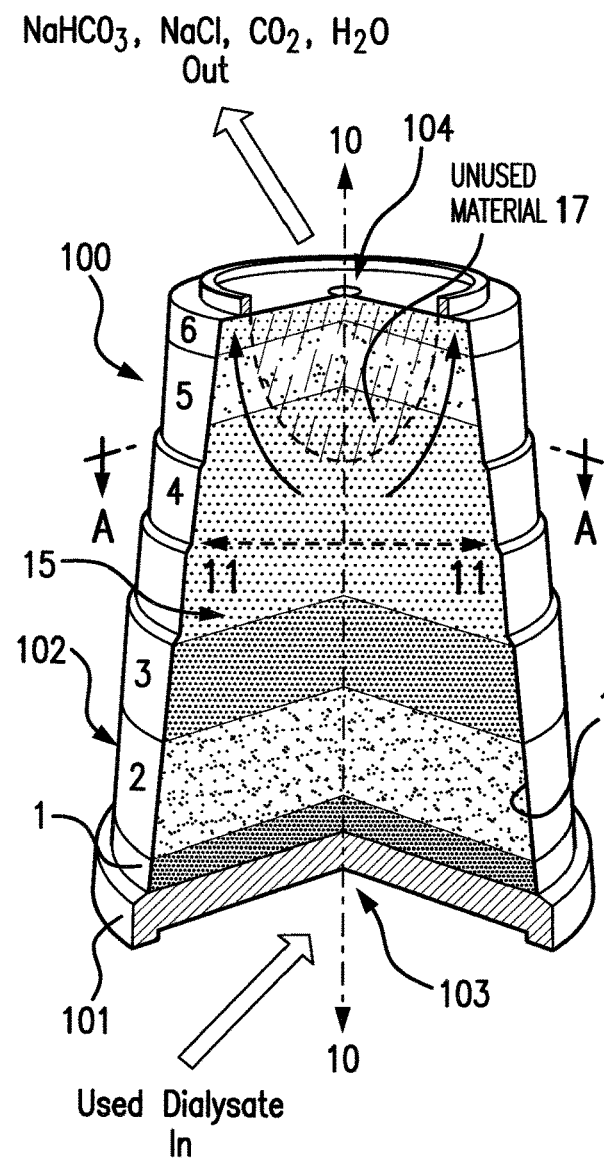

| | Binds | | Releases |
|---|---|---|---|
| | Nothing | 6 | Sodium bicarbonate |
| | Phosphate Fluoride Anionic metal complexes Other Anions | 5 | Chloride Hydroxide |
| | Ammonium Calcium Magnesium Potassium Metals Cationic metal complexes Other cations | 4 | Sodium Hydrogen |
| | Oxidants Chloramines Uric acid Other organics Middle molecules | 3 | Nothing |
| | Nothing– converts Urea | 2 | Ammonium bicarbonate |
| | Oxidants Chloramines Uric acid Other organics Middle molecules | 1 | Nothing |

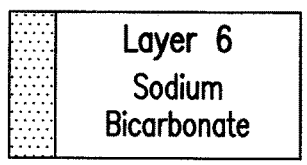
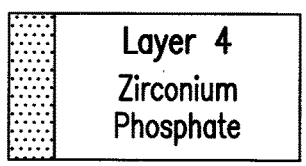
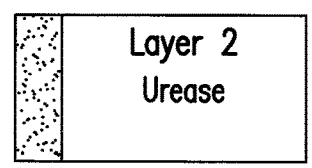
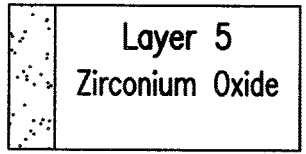
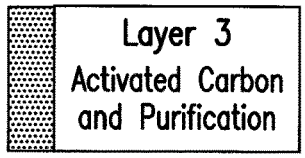
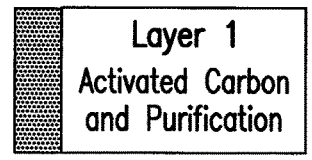

PRIOR ART
FIG. 3

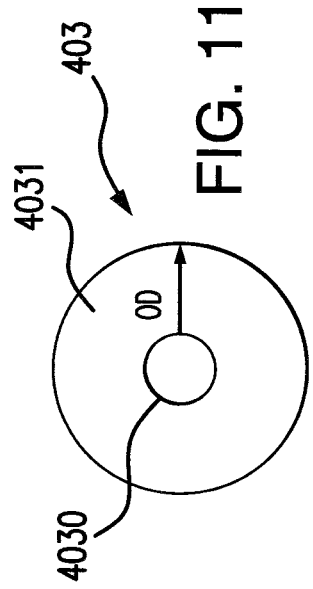
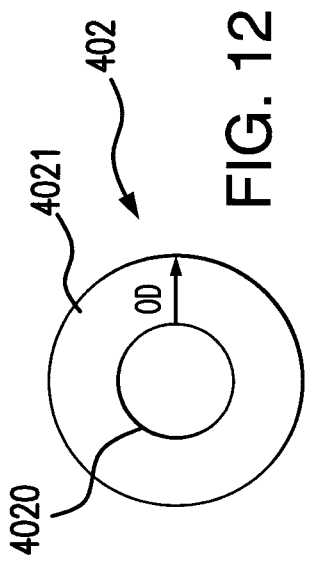
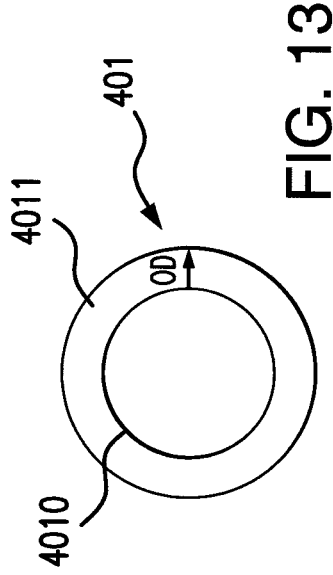
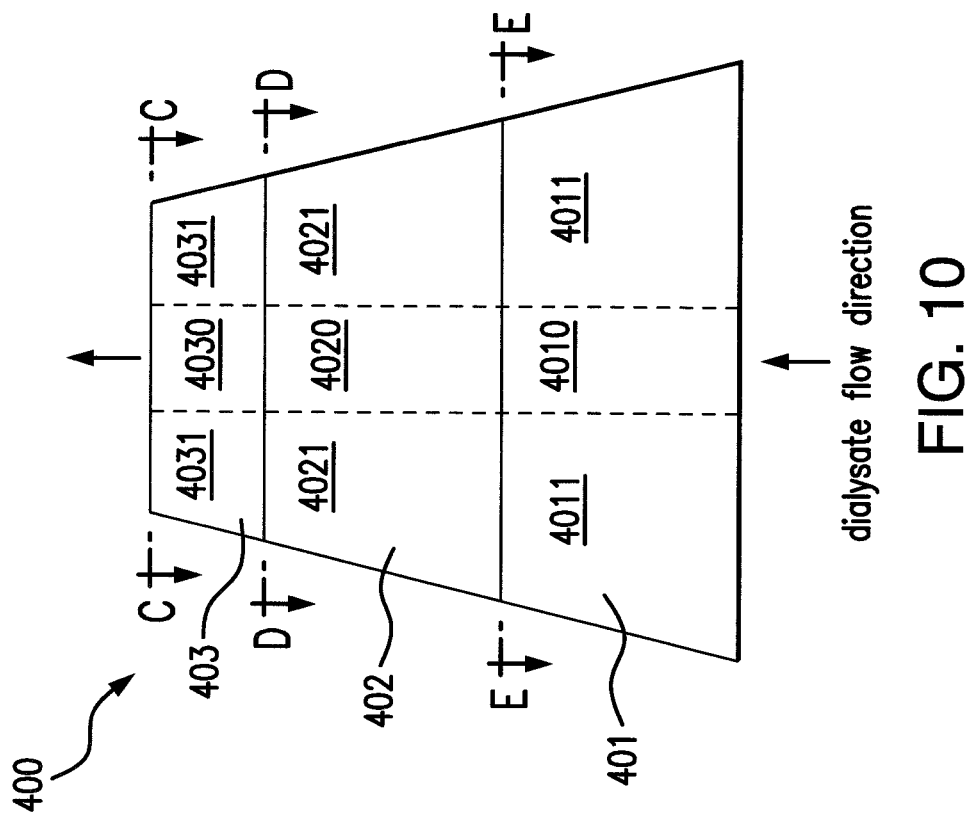

CARTRIDGES USEFUL IN CLEANING DIALYSIS SOLUTIONS

This application is a National Stage Application of PCT/US2016/043442, filed Jul. 22, 2016, which claims the benefit under 35 U.S.C. § 119(e) of prior U.S. Provisional Patent Application No. 62/219,369, filed Sep. 16, 2015.

BACKGROUND OF THE INVENTION

The present invention relates to cartridges such as ion exchange cartridges or adsorption cartridges which are useful, for instance, in dialysis. In particular, the present invention relates in general to the regeneration or purification of used dialysate fluids. The present invention further relates to methods of conducting dialysis using certain cartridges.

Dialysis is a treatment that removes the waste products and excess fluid that accumulate in the blood as a result of kidney failure. Chronic renal failure is when the renal function has deteriorated to about 25% of normal. This amount of deterioration causes significant changes in the blood chemistry and is about the time that people feel poorly enough that they seek medical care. Peritoneal dialysis (PD) is one form of dialysis. With this treatment, a mild saltwater solution containing dextrose and electrolytes called dialysate is put into the peritoneal cavity. Because there is a rich blood supply to this abdominal cavity, urea and other toxins from the blood and fluid are moved into the dialysate, thereby cleaning the blood. The dialysate is then drained from the peritoneum. Later "fresh" dialysate is again put into the peritoneum.

Also, there is hemodialysis. This is a method of blood purification in which blood is continually removed from the body during a treatment session and passed through a dialyzer (artificial kidney) where metabolic waste and excess water are removed and pH and acid/base balances are normalized. The blood is simultaneously returned to the body. The dialyzer is a small disposable device consisting of a semi-permeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit which acts to pump and control pressures, temperatures, and electrolyte concentrations of the blood and the dialysate. The average length of one hemodialysis treatment is 3-5 hours.

There are several types of hemodialysis:
a) Single Pass—hemodialysis is the most common treatment for renal disease. Most hemodialysis treatments are performed with single pass dialysis machines. They are called single pass because the dialysate (cleaning solution) passes by the blood in the dialyzer one time and then is disposed. Single pass dialysis machines generally require:
1) a water source capable of delivering at least 1000-1500 ml/min (assuming a 50% rejection rate by the reverse osmosis ("R.O.") system)
2) a water purification system sufficient of providing a continuous flow of 500-800 ml/min of purified water.
3) an electrical circuit of at least 15 amps in order to pump and heat 500-800 ml of water/min.
4) a floor drain or any other receptacle capable of accommodating at least 500 ml of used dialysate/minute as well as the rejected water from the R.O. system.

b) Sorbent Dialysis—does not require a continuous water source, a separate water purification machine or a floor drain because it continuously regenerates a small volume of dialysate and incorporates a water treatment system within the machine. Therefore, sorbent systems are more portable.
1) sorbent systems typically require only a 5 amp electrical source because they recycle the same small volume of dialysate throughout the dialysis procedure. The heavy duty dialysate pumps and heaters used for large volumes of dialysate in single pass dialysis are not needed.
2) the sorbent system can use 6-12 liters of tap water from which dialysate is made for an entire treatment.
3) the sorbent system uses a sorbent cartridge—which acts both as a water purifier and as a component to regenerate used dialysate into fresh dialysate. The infusate system acts with it to properly balance the electrolyte composition of the regenerated dialysate.

The sorbent cartridge containing zirconium phosphate (ZrP) and hydrous zirconium oxide (HZO) ion-exchange materials has been historically used for the REDY regeneration hemodialysis system. The scheme of the REDY cartridge is shown in FIG. 1. The sorbent cartridge is shown with the inlet and the outlet identified as numeral 11 and numeral 13, respectively. FIG. 2 shows various functions of each layer in a REDY cartridge.

The principle of the REDY cartridge is based on the hydrolysis of urea to ammonium carbonate by the enzymatic reaction of urease. The following equation shows a reaction for urea conversion to ammonia in the presence of urease:

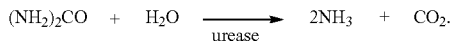

The ammonia and ammonium ions are then removed by the zirconium phosphate in exchange for the hydrogen ions and $Na^+$ ions, which are counter-ions in the cation exchanger. Zirconium phosphate also serves as cation exchanger to remove Ca, Mg, K, and all toxic metals in dialysate, thus allowing a balance of electrolyte level in the patient's blood (Ca, Mg, K) to be maintained by using an infusate system, as well as providing safety for dialysis treatment with regard to water quality. The carbonate from the urea hydrolysis then combines with the hydrogen ions in zirconium phosphate to form bicarbonate, which is delivered to the uremic patient as a base to correct for acidosis. Zirconium phosphate can be represented as inorganic cation exchange material with the molecular structure as shown below:

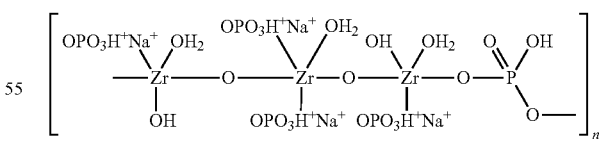

As shown, the material contains both $H^+$ and $Na^+$ as counter-ions, which are responsible for ion exchange. The relative content of these ions can be controlled by the pH to which acid ZrP (or $H^+ZrP$) is titrated with NaOH. The composition of the resultant product of titration, $Na_x^+H_{2-x}^+ZrP$ (or abbreviated as "NaHZrP" herein), may vary during ion exchange processes in dialysate. The hydrous zirconium oxide (HZO) containing acetate (HZO.Ac) as a counter ion serves as an anion exchanger to remove phosphate. The material also prevents leaching of phosphate from NaHZrP and removes toxic anions (e.g., fluoride) in water that may cause harm to a patient during dialysis. The acetate released during ion exchange is also a base to correct for acidosis by acetate metabolism. The compositional formula of hydrous zirconium oxide (HZO) can be $ZrO_2 \cdot nH_2O$ (i.e. zirconium oxide hydrate) or $ZrO_2 \cdot nOH \ldots H^+An^-$ in the anion form wherein Ad is an anion attached to HZO, such as acetate ("Ac"), chloride, etc. Without the anion, it can be considered as partially oxalated zirconium hydroxide with various degrees of $O^{2-}$, $OH^-$ and $H_2O$ bonded to Zr, i.e., $Zr(OH)_xO_y(H_2O)_z$. The granular activated carbon in the cartridge is used in the REDY cartridge for the removal of creatinine, uric acid, and nitrogenous metabolic waste of the patient as well as chlorine and chloramine from water.

As indicated, a sorbent cartridge usually includes multiple layers that comprise a similar or substantially chemical composition in each given layer. Flow distribution in a given cartridge layer of the sorbent cartridge can vary across the layer. Channeling phenomenon can occur in a peripheral region of a cartridge layer or layers of a cartridge that are located nearer to the cartridge wall. Fluid flow can increase in the peripheral region of a layer or layers at the expense of a central region thereof located further from the cartridge wall. This is undesirable as it can result in separate regions of overly-used material and unused (or underused) material in the same layer of the cartridge. This can lead to inefficient treatment performance, early or premature exhaustion of a cartridge component, shortening of the useful life of cartridge, unused material in the spent cartridge, or combinations of these problems. Sorbent cartridge designs would be preferred that can further reduce or prevent variations in flow distribution from occurring in the sorbent cartridge. Accordingly, in the area of dialysis, it would be beneficial to overcome one or more of the above-described disadvantages.

SUMMARY OF THE PRESENT INVENTION

A feature of the present invention is to provide cartridge configurations having improved flow distribution therein, which are useful in the regeneration or purification of solutions, such as solutions containing waste products and/or impurities.

A further feature of the present invention is to provide cartridge configurations with more uniform flow distribution therein, which are useful in the regeneration or purification of dialysis solutions such as hemodialysis or peritoneal dialysis solutions or other dialysate solutions.

A further feature of the present invention is to provide a sorbent cartridge for regenerating or purifying spent dialysis fluid which can reduce non-uniform flow distribution in dialysate fluids flowing through one or more solid particulate layers of the sorbent cartridge.

A further feature of the present invention is to provide methods to regenerate or purify spent dialysis fluids which can use such sorbent cartridges such as to improve the performance efficiency and reduce the amount of unused cartridge material.

A further feature of the present invention is to provide dialysis systems which can regenerate or purify spent dialysis fluids with such sorbent cartridges.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, the present invention relates to a sorbent cartridge, that at least includes a continuous sidewall extending between a first end wall and a second end wall, which define a chamber; at least first and second layers, wherein the at least first and second layers extend across the chamber within the continuous sidewall, wherein at least one of the first and second layers include a first region, a second region adjacent the first region and located closer to the continuous sidewall than the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density (e.g., when at least the first and second layers are wet).

The present invention further relates to a sorbent cartridge, that includes a) a continuous sidewall extending between a first end wall comprising an inlet and a second end wall comprising an outlet, which define a chamber; b) an enzyme-comprising layer; c) a zirconium phosphate-containing layer that follows the enzyme-comprising layer within the sorbent cartridge, wherein the zirconium phosphate-containing layer includes a first region, a second region adjacent the first region and located closer to the continuous sidewall than the first region, first solid particulate media in the first region having a first packing density, second solid particulate media in the second region having a second packing density, and a packing density differential between first solid particulate media in the first region and the second solid particulate media in the second region wherein the first packing density is less than the second packing density (e.g., when at least the first and second solid particulate media are wet).

The present invention also relates to a method of making a sorbent cartridge, that includes a) forming an enzyme-comprising layer that extends across a chamber defined by a continuous sidewall of the sorbent cartridge; b) forming a solid particulate media-containing layer having a packing density differential that follows the enzyme-comprising layer within the sorbent cartridge, comprising i) depositing solid particulate media as a starting layer on the enzyme-comprising layer, wherein the starting layer comprises a first region, a second region adjacent the first region and located closer to the continuous sidewall than the first region, ii) applying a first vibrational or mechanical force to the first region that is less than a second vibrational or mechanical force applied to the second region which results in first solid particulate media in the first region having a first packing density and second solid particulate media in the second region having a second packing density, wherein the first packing density is less than the second packing density.

The present invention, in addition relates, to just the layer arrangement and packing density differential mentioned above in the absence of a sidewall.

The present invention also relates to a method to regenerate or purify spent dialysis, fluid that includes passing spent dialysis fluid through one of the sorbent cartridges described herein.

The present invention further relates to a dialysis system to regenerate or purify spent dialysis fluid that includes one of the sorbent cartridges described herein.

It is to be understood that both the foregoing general description and the following detailed description are exemplary and explanatory only and are intended to provide a further explanation of the present invention, as claimed.

The accompanying drawings, which are incorporated in and constitute a part of this application, illustrate several embodiments of the present invention and together with the description, serve to explain the principles of the present invention.

BRIEF DESCRIPTION OF THE DRAWINGS

The drawings represent various design features of the sorbent cartridges of the present invention and comparison designs. Similar referencing identifiers in different figures can refer to similar features unless indicated otherwise. The drawings are not necessarily to scale.

FIG. 3 is an exploded view of materials in a comparison example of a sorbent cartridge which has nonuniform flow distribution through layers thereof. Various intended functions of each layer of the cartridge are indicated.

FIG. 10 is an exploded view of materials in one example of a sorbent cartridge which has a packing density differential provided in multiple layers thereof according to an example of the present application.

FIG. 11 is a top plan view in direction C-C of the sorbent cartridge shown in FIG. 10.

FIG. 12 is a top plan view in direction D-D of the sorbent cartridge shown in FIG. 10.

FIG. 13 is a top plan view in direction E-E of the sorbent cartridge shown in FIG. 10.

DETAILED DESCRIPTION OF THE PRESENT INVENTION

Figure 1:
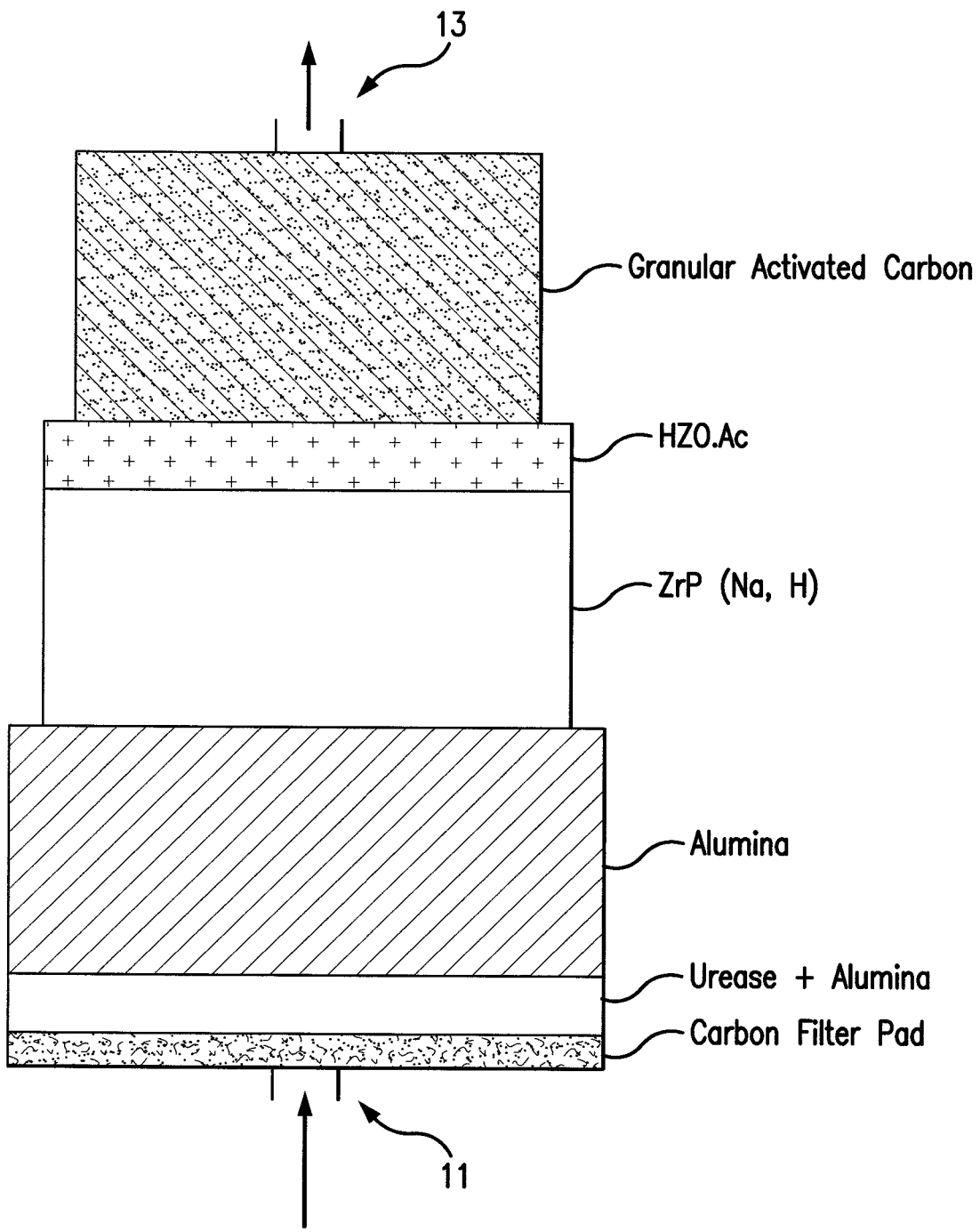
FIG. 1 is a schematic diagram showing a REDY® cartridge.
Figure 2:
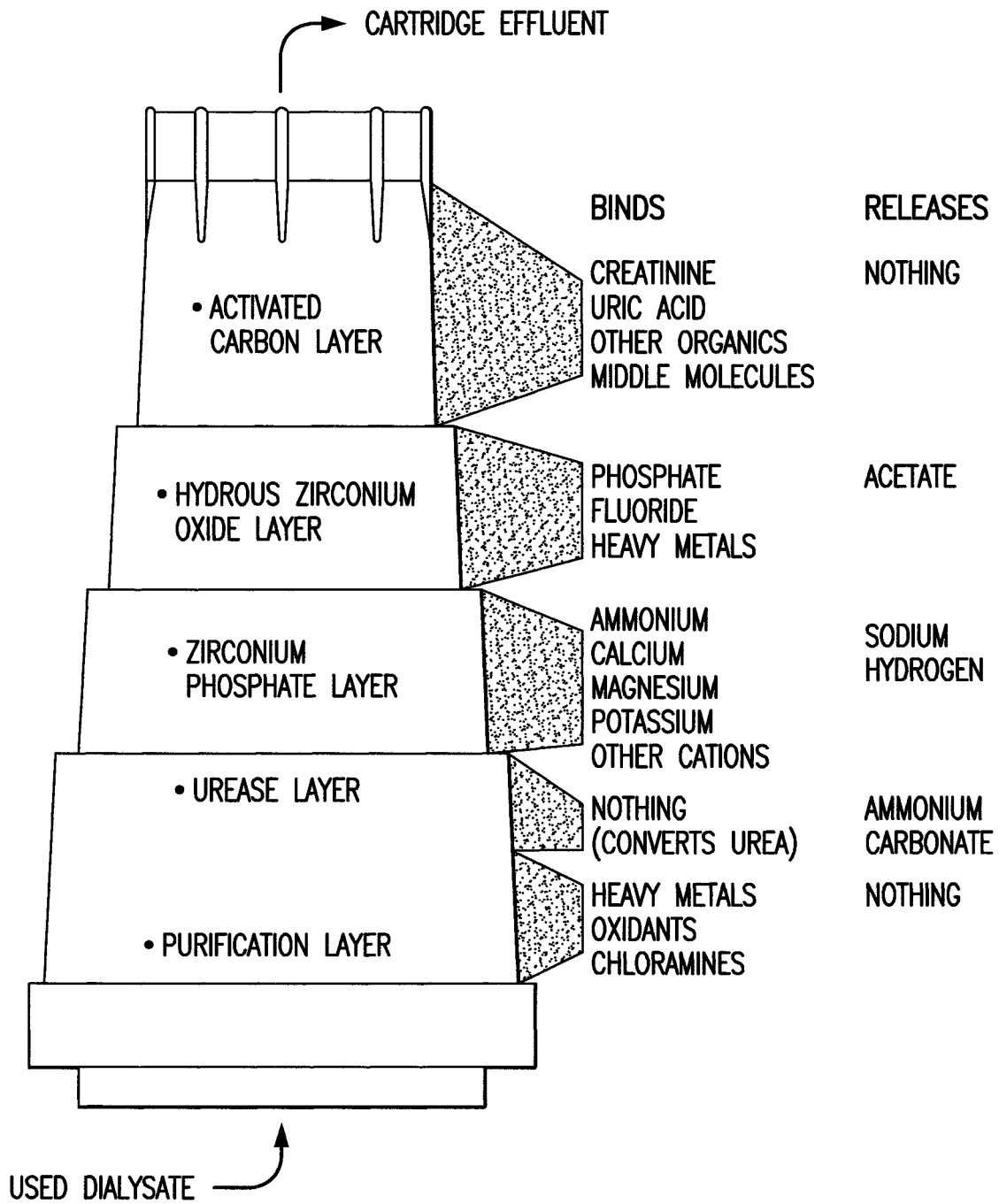
FIG. 2 is a diagram showing a cartridge and the various functions of each layer in a REDY® cartridge.

The present invention relates to cartridge configurations for separation processes, such as the removal of waste products and excess fluid that accumulates in dialysate fluids, which can incorporate a packing density differential to provide improved flow distribution therein. As an option, one or more of packed bed particle layers in a sorbent cartridge can be differentially packed with particles wherein an outer or peripheral region of the one or more layers has a greater packing density than an inner or central region of the same layer or layers, wherein hydraulic pressure and therefore the flow distribution through the one or more layers can be made uniform or substantially uniform. This can provide improved efficient performance and/or avoid early or premature exhaustion of the cartridge. These improved configurations can comprise packed bed particle and any other layered materials present in a container (i.e., a cartridge) capable of holding the layered materials useful for the separation process, wherein at least one or more or all of the particle bed containing layers present have a packing density differential as described herein. As an option, the packed bed particle and other layered materials described in detail below or the arrangement of various layered materials can be used in a dialysis system or other similar type of system that is useful for the removal of waste products and/or excess fluid that accumulates in dialysate fluids, for instance, as a result of conducting dialysis. As described in more detail below, the present invention is useful in purifying or regenerating dialysate fluids used in peritoneal dialysis (PD) and in hemodialysis (HD). For purposes of the present invention, a dialysis solution means a peritoneal dialysis solution or dialysate fluids that are useful in hemodialysis or sorbent dialysis systems. Conventional dialysis solutions for PD or HD can be used and regenerated by the present invention and are known to those skilled in the art.

A sorbent cartridge which includes one layer(s) that is formed by a packed bed of solid particles of the same or substantially similar chemical composition (e.g., same chemical formula or analogs thereof or derivatives thereof), can have less than desired performance at times. Flow distribution in such a cartridge layer(s) can be non-uniform due to variations in hydraulic pressure and thus flow velocity in different parts of the layer. The peripheral region of a packed bed of particles forming a cartridge layer that is located nearer to the cartridge wall than a central region of the same layer can be more liquid permeable. As a result, the liquid flowing through the cartridge therefore can tend to flow more through the peripheral region where there is less resistance to flow as compared to the central region wherein it is relatively more difficult for the fluid to penetrate. This can result in unused (or underused) material in the central region of the layer of the cartridge, whereas the peripheral region nearer to the cartridge wall can have overly-used material. This can lead to early or premature exhaustion of a cartridge component. For instance, flow distribution can be nonuniform in a layer of zirconium phosphate particles in a sorbent cartridge wherein a peripheral region of the layer is subjected to greater flow and thus greater usage than a central region of the same layer. If this occurs, ammonia breakthrough for the cartridge can occur earlier than if flow distribution had been uniform across the layer, thus shortening the useful life of the cartridge. Compounding this drawback, unused material, e.g., 10% to 15% by volume or other amounts, can be left in the layer or layers of the sorbent cartridge to be discarded. Sorbent cartridge designs would be preferred that can further reduce or prevent variations in flow distribution from occurring in packed bed particle layers of the sorbent cartridge. Accordingly, in the area of dialysis, it would be beneficial to overcome one or more of the above-described disadvantages associated with use of particles of similar kinds, sizes and morphologies arranged in a similar packing mode throughout a packed bed particle layer (or in multiple layers of the cartridge).

FIG. 3 shows a sorbent cartridge of a comparison example that is being used for treatment of dialysate fluid, which experiences differential hydraulic pressure and fluid flow through different regions of several layers of packed bed materials in the cartridge. The sorbent cartridge is identified in FIG. 3 as component 100, which has a housing 101, which comprises a solid continuous sidewall 102, inlet end wall 103, and outlet end wall 104, and a multi-layered sorbent bed 15 is incorporated within the housing 101. The sorbent bed 15 is shown here comprised of layers 1-6 and a central longitudinal axis 10-10, which extends through the sorbent bed 15 (usually coinciding with or near the geometric center of sorbent bed layers 1-6). The sorbent bed layers 1-6 extend in directions 11 radially outward (and usually orthogonally or substantially orthogonally (e.g., within 1 to 10 degrees of orthogonal)) from the central longitudinal axis 10-10 to an inner face (wall) 105 of the continuous sidewall 102 of the housing 101. In this configuration, each of layers 1-6 of the sorbent cartridge are comprised of material of similar chemical composition and physical properties per layer (e.g., particle size distribution, morphology, crystallinity and/or other properties). The particles used in these layers can be originally supplied in freely flowable solid particulate form. Once incorporated into the respective layers in the cartridge they are packed into layered beds comprising strata formed of the particles. Hydraulic pressure in the cartridge usually increases from layer to layer in the indicated direction of fluid flow through the sorbent cartridge, as expected from principles of hydraulics. In particular, there can be an uneven flow distribution within of one or more of the individual cartridge layers that comprise a packed bed of particles. In the sorbent bed shown in FIG. 3, all or any lesser combination of layers 1-6 can be comprised of a packed bed of particles. These layers are shown here for sake of illustration, and other layers may be present in the alternative or in addition, or omitted from the cartridge. For purposes of this comparison example, at least the layer 4 is present and comprised of a packed bed of particles.

With regard to the cartridge of the comparison example shown in FIG. 3, a problem can occur wherein one or more of the individual layers of particles of the same or similar composition have a same or similar packed bed composition, particle distribution, crystallinity, and packing mode throughout the layer (e.g., within 10% for one or more of these properties), such as in a radial direction from a geometric center of the layer all the way to a peripheral edge thereof. If so, hydraulic pressure can be less in a peripheral region of the packed bed of particles forming at least one of the layers in the sorbent cartridge (e.g., a region nearer to the cartridge wall) as compared to a hydraulic pressure at the central region of the same layer that is located closer to the central axis of the cartridge. The fluid flow encounters less resistance to flow in the peripheral regions of layer or layers 4-6 as compared to the central region of the cartridge. This is undesirable as fluid flow can be channeled into the peripheral regions of layer 4-6 and diverted at least partially, essentially completely, or completely away from the central regions of these layers. This phenomenon is indicated by the arrows representing fluid flow directions that are shown in FIG. 3. This can result in unused (or underused) material 7 in the central region of at least one layer of the cartridge, whereas the peripheral region nearer to the cartridge wall can have overly-used material which becomes exhausted prematurely. This can impair the treatment performance and/or efficiency (e.g., urea capture efficiency) of the sorbent cartridge. The useful life of the cartridge can be shortened.

In FIG. 3, the region of unused material 7, which is identified by cross-hatching, has a parabolic profile that extends completely through layers 5 and 6 and partially through layer 4. This profile of the unused material is exemplary and not limited thereto. The unused material can be an amount, such as from about 10% to about 15% by volume or other amounts based on the volumes of any one or more of the indicated packed bed particle layers, and/or can have any geometric profile in the cartridge.

Figure 4:
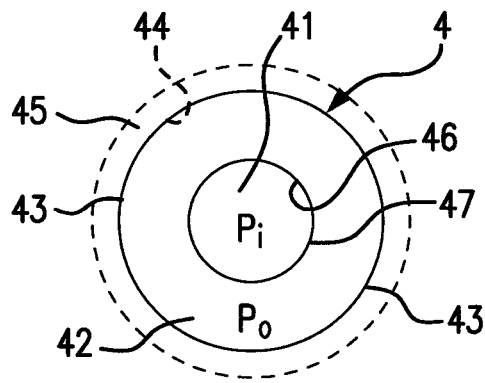
FIG. 4 is a top plan view in direction A-A of the sorbent cartridge shown in FIG. 3.

FIG. 4 shows a hydraulic pressure $P_i$ in a central (inner) region 41 of layer 4 and pressure $P_o$ in the peripheral or outer region 42 of layer 4 in the sorbent configuration of FIG. 3 that has the indicated channeling problem. In this comparison example, the particles used to form layer 4 have the same particle size distribution and morphology throughout the cross-sectional area of the layer. The starting packing density of the constituent particles of layer 4 is the same throughout layer 4 including in the peripheral region 42 and the central region 41. The outer edge 43 of peripheral region 42 is contiguous with an inner face 44 of a sidewall 45 of the cartridge housing. During fluid flow through the sorbent cartridge 4, $P_o$ is or becomes less than (<) $P_i$ in a sufficient amount that fluid flows preferentially through the peripheral region of the layer as compared to fluid flow, if any, through the central region thereof. $P_o$ can represent a pressure that is present through all or essentially all (e.g., at least 75%, or 80%, or 90% by volume) of the packed bed of particles in outer region 42 which accommodates fluid flow completely through the layer. $P_i$ can represent a pressure that is present through all or essentially all (e.g., at least 75%, or 80% or 90% by volume) of the packed bed of particles in central region 41 which does not accommodate fluid flow through the central region 41. The outer region 42 has an inner edge 46 that is adjacent and contiguous with an outer edge 47 of the central region 41 that it encircles. In the arrangement of FIG. 4, the inner edge 46 of the outer region 42 completely surrounds the central region 41. FIG. 4 shows the peripheral and central regions (42, 41) arranged as concentric circles. Other cartridge shapes can encounter similar differential flow problems in the sorbent bed as the cartridge having the geometry shown in FIGS. 3 and 4.

Figure 5:
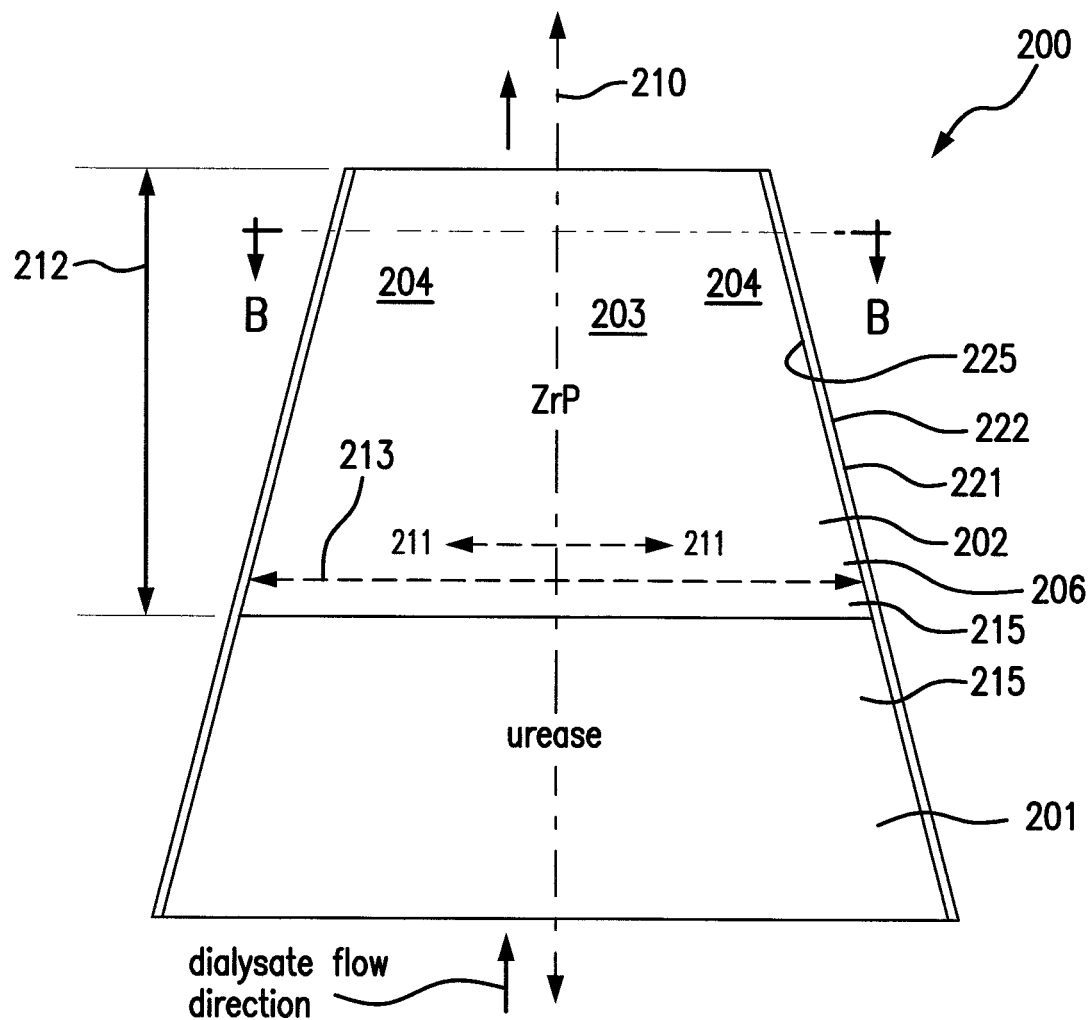
FIG. 5 is an exploded view of materials in one example of a sorbent cartridge which has a packing density differential provided in a zirconium phosphate layer thereof according to an example of the present application.

Referring to FIG. 5, a sorbent cartridge 200 according to an example is shown that includes a layer 201 (e.g., urease layer 201) and layer 202 (e.g., zirconium phosphate layer 202). These layers are shown here for sake of illustration, and the concepts described herein are not at all limited to these layers or types of layers. Sorbent cartridge 200 may include additional treatment and other functional layers not shown in this illustration. The sorbent cartridge 200 has a central axis 210 that extends through the layers 201 and 202 and any other layers in the cartridge (usually coinciding with or near the geometric center of sorbent bed layers 201-202). The central axis 210 extends longitudinally through the geometric center of the shape of the cartridge housing 221 defined by its continuous sidewall 222. The sidewall 222 forms a continuous enclosure around the outer edges of the layers incorporated within the cartridge. The first and second sorbent layers 201 and 202 can be centered about central axis 210. The layers 201 and 202 can be centered in the cartridge with respect to the central axis 210. The sorbent bed layers 201 and 202 extend in directions 211 radially outward (and usually orthogonally or substantially orthogonally) from the central axis 210 to an inner face 225 of a continuous sidewall 222 of the cartridge housing 221. The cartridge 200 can have an inlet end wall and outlet end wall (not shown) similar to housing 100 shown in FIG. 3, or can have other designs. Each of layers 201 and 202 can be formed of particles shaped into a disc-shaped component having an overall thickness that is uniform or substantially uniform throughout the respective layer, and a diameter in the radial direction which, in this example, gradually decreases through the thickness of the respective layer in the direction of fluid flow with respect to the central axis 210. Layer 202, for example, is shown in FIG. 5 with thickness 212 (vertical) and a diameter 213 (radial). Layers 201 and 202 together can be referred to as a sorbent bed 215 for purposes of this illustrated cartridge.

In the cartridge configuration shown in FIG. 5, layers 201 and 202 of the sorbent cartridge are each comprised of material of the same or similar chemical composition for that layer, whereas layer 202 also is a composite layer which has different regions having different packing densities with respect to each other. In one option, the packing densities are differentially selected with respect to each other depending on the proximity of the respective region to the central region (e.g., far from wall) and peripheral region (e.g., near wall) locations of layer 202. Hydraulic pressure in a cartridge, such as shown in FIG. 5, usually increases from layer to layer in the indicated direction of fluid flow through the sorbent cartridge, as expected from hydraulic principles. In addition, it has been found that a wall effect of the housing 221 on the packed bed layer 202 can result in reduced flow resistance in the outer or peripheral region 204 of layer 202 as compared to the inner or central region 203 of layer 202. If not countered or compensated for, the wall effect can lead to the indicated channeling of flow through the outer region 204 at the expense of flow through the inner region 203 of layer 202. As an option, in the sorbent bed 215 shown in FIG. 5, the particles in inner region 203 of layer 202 have a packing density ($D_{p1}$) that is less than the packing density ($Dp_2$) of the particles in outer region 204 of layer 202. The packing density therefore varies in layer 202 in a radial direction extending from a geometric center of the layer (e.g., coinciding with central axis 210) towards a peripheral edge 206 of layer 202.

To provide a packing density differential in layer 202, the respective particles in central region 203 and peripheral 204 of layer 202 can be incorporated into the cartridge having different physical properties, e.g., particle size distribution, packing mode, crystallinity and/or other properties, which can be differentiated in the particles as between the peripheral and central regions of the layer to provide different impedance or resistance to hydraulic flow in different regions of layer 202. Smaller particles, for example, can pack more tightly than larger particles, all other things equal, and therefore can provide a greater packing density relative thereto. Smaller sized particles can be used in the peripheral region 204 as compared to the particle sizes used in the central region 203 to provide greater (tighter) packing density in the peripheral region 204 relative to the central region 203 of layer 202. Further, particles of a sieve cut having a smaller size distribution than particles of another sieve cut can pack more tightly, all other things equal, and therefore can provide a greater packing density relative thereto. A sieve cut of particles can be used in the peripheral region 204 as compared to a sieve cut used in the central region 203 to provide a range of particle sizes in the peripheral region 204 that is smaller than the range of particle sizes in the central region 203, which can provide a greater (tighter) packing density in the peripheral region 204 relative to the central region 203 of layer 202. In this option, the sieve cut used for the central region can comprise a particle size range that comprises at least one particle size that is larger than all the particle sizes of a sieve cut used for the peripheral region. If not available commercially, a standardized mesh screen series can be used to isolate different sieve cuts from a supply of particles to be used in a layer of the sorbent cartridge that is being provided with a packing density differential. As an example, a first sieve cut can be obtained from a supply of the particles for use in the central region 203 of the layer 202 which can be −140+230 mesh (U.S. mesh, i.e., less than 0.105 mm and more than 0.063 mm), and a second sieve cut can be obtained from the same or a similar supply of particles for use in the peripheral region 204 of the layer 202 that can be −270+400 U.S. mesh (U.S. mesh, i.e., less than 0.053 mm and more than 0.037 mm). Other ranges of values of particle sizes can be used for the second sieve cut used in region 204 that are smaller partially or completely as compared to the size range of the particles of the first sieve cut used in region 203. The following convention is used to characterize particle size by mesh designation: "+" before the sieve mesh indicates the particles are retained by the sieve; a "−" before the sieve mesh indicates the particles pass through the sieve; typically 90% or more and up to 100% by number of the particles can lie within the indicated range. For example, if the particle size of a material is described as −140+230 mesh (US), then 90% or more up to 100% by number of the material will pass through a 140-mesh sieve (particles smaller than 0.105 mm) and be retained by a 230-mesh sieve (particles larger than 0.063 mm). The use of different sieve cuts for the central and peripheral regions that have partially overlapping range values for the particle sizes may be used provided that at least some of the particles in the sieve cut used in the central region are larger than all of the particles in the other sieve cut used in the peripheral region. In another example, the particle size ranges of the first and second sieve cuts do not overlap at all.

As another option, from about 90% to about 92% by number of solid particles used in the peripheral region 204 can be finer than solid particles in the central region 203 and from about 8% to about 10% by number of the solid particles used in the central region 203 can be finer than the solid particles in the peripheral region 204. As an option, a D10 particle size distribution fraction of a supply of particles can be used in the peripheral region 204 of layer 202 and the rest of the particles can be used in the central region 203 thereof. A D10 diameter is the diameter at which 10% of a particulate sample's mass is comprised of smaller particles. As used herein, a D10 fraction refers to a fraction composed of those smaller particles. The remaining fraction that is not the D10 fraction can be used in the central region 203. Instead of a D10 fraction, any fraction from D5 to D30 can be used as the particles for the peripheral region, such as D5, D10, D15, D20, D25 or D30. The remaining fraction that is not the D fraction used in the peripheral region can be used in the central region.

Particles packed using a bimodal or multimodal packing technique (a bimodal or multimodal particle distribution)

also can provide a greater packing density than a bed of particles made with only one size of particle. Bimodal and multimodal packing, for example, can use fine particles to fill in interstitial spaces between larger packed particles, which can result in greater packing density than possible with any one of the constituent particle sizes used alone. A bimodal or multimodal bed of particles can be used in the peripheral region 204 as compared to a unimodal or non-modal bed used in the central region 203, which can provide a greater (tighter) packing density in the peripheral region 204 relative to the central region 203 of layer 202.

The peripheral region can be from 1% to 50% of the cross-sectional area of the layer, such as 1%, 5%, 10%, 15%, 20%, 25%, 30%, 35%, 40%, 45% or 50%. The central region can be from 10% to 80% of the cross-sectional area of the same layer, such as 10%, 15%, 20%, 25%, 30%, 35%, 40%, 45%, 50%, 55%, 60%, 65%, 70%, 75%, or 80%.

The average packing density in the central region compared to the peripheral region can vary by at least 5%, at least 10%, at least 15%, at least 20%, at least 25%, at least 30%, at least 40%, at least 50%, at least 75%, at least 100%, at least 200%, where the central region has a lower packing density than the peripheral region.

As another option, different particle crystallinities can inversely correlate with different magnitudes of wet particle swellabilities. For example, different sources of zirconium phosphate particles can be commercially obtained or prepared which have different crystallinities. Zirconium phosphate particles that have different crystallinities can be commercially obtained, generally, from zirconium phosphate manufacturers or suppliers, or can be made by a preparation technique which comprises chemical processing. For particles that can have a crystalline morphology, particles of the same chemical composition and size that have greater crystallinity than other particles of the same chemical composition and size can not swell as much when wetted. Particles having a lower crystallinity can be used in the peripheral region 204 as compared to particles having greater crystallinity used in the central region 203, which can provide a greater (tighter) packing density in the peripheral region 204 relative to the central region 203 of layer 202 when the packing material is in a wet operational state.

A peripheral region 204 that has a greater packing density than the central region 203 also can be formed in-situ. For example, a sorbent cartridge can be made by forming an enzyme-comprising layer (e.g., urease layer) that extends across a chamber defined by a continuous sidewall of the sorbent cartridge, and then forming a solid particulate media-containing layer (e.g., a zirconium phosphate layer or other particle layer) having a packing density differential that follows the enzyme-comprising layer within the sorbent cartridge, wherein the packing density differential is not formed in the solid particulate media-containing layer until after the particles of the layer have already been deposited on the enzyme-comprising layer. The solid particulate media can be deposited as a starting layer on the enzyme-comprising layer, wherein the starting layer comprises a central region and a peripheral region adjacent the central region and located closer to the continuous sidewall than the central region. At this stage of production, the central and peripheral regions can still have the same packing density. Then, a vibrational force or mechanical force is applied to the cartridge loaded with the materials wherein the particles in the central region receive less vibrational or mechanical force than the vibrational force applied to the peripheral region, which results in the particles in the central region having a packing density that is less than the packing density of the particles in the peripheral region. As an option, an ultrasonic device, such as one or more ultrasonic transducers or horns, can be arranged to apply greater vibrational force to the particles in the peripheral region as compared to the particles central region wherein the particles in the peripheral region pack more tightly than those in the central region. One or more ultrasonic horns may be arranged in contact with the outer periphery of the cartridge housing where adjacent to the outer region of a packed bed particle layer positioned inside the cartridge wherein greater vibrational force is applied to peripheral region of the particle layer than the more distant central region thereof.

By using one or more of these indicated techniques or others for providing a packing density differential in layer 202, a packing density ($Dp_1$) of the central (inner) region 203 can be made sufficiently lower than the packing density ($Dp_2$) of the peripheral (outer) region 204 to offset or substantially offset wall effect on fluid flow in the outer region 204 to reduce or eliminate channeling phenomenon in the layer. Packing density usually is positively correlated with the magnitude of hydraulic pressure that occurs in the respective region of the layer in use. Higher packing density correlates with higher hydraulic pressure and relatively lower packing density correlates with lower hydraulic pressure. By differentially varying the packing densities in separate regions of the same layer, differential hydraulic pressure can be provided in the layer that is greater in a peripheral region of the packed bed of particles forming the layer in a sorbent cartridge (e.g., a region nearer to the cartridge wall) as compared to a hydraulic pressure at the central region of the same layer that is located further away from the cartridge wall and closer to the central longitudinal axis of the cartridge. The fluid flowing through the cartridge therefore can encounter similar or substantially similar resistance to flow in the peripheral region 204 as compared to the central region 203 of the cartridge. In this way, in sorbent bed configurations described herein, the fluid flow can be enabled to occur simultaneously through inner region 203 and outer region 204 of layer 202 and at similar or substantially similar hydraulic pressures and flow rates therethrough. This can reduce the occurrence of unused (or underused) material in the central region of layer 202 of the cartridge, and reduce the risk of the cartridge materials being exhausted prematurely, as compared to a similar cartridge design that differs by using a zirconium phosphate layer 102 having the same packing density through the layer. This can improve treatment performance and/or efficiency (e.g., urea capture efficiency) of the sorbent cartridge.

The amount of any unused material in layer 202 of the sorbent cartridge 200 can be reduced as compared to a similar cartridge design that differs by using a layer 102 having the same packing density throughout the layer. The unused material in a particle bed containing layer having a packing density differential such as indicated in a sorbent cartridge described herein can be reduced to 5% or less by volume, such as from 0 to about 5% by volume, or from about 1% to about 5% by volume, or from about 1% to about 4% by volume, or from about 1% to about 3% by volume, or other amounts, based on volume of the indicated packed bed particle layer.

Figure 6:
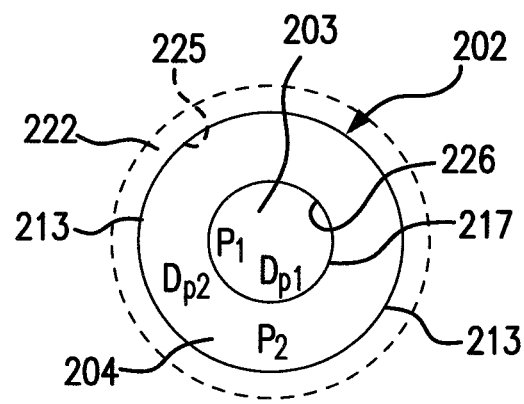
FIG. 6 is a top plan view in direction B-B of the sorbent cartridge shown in FIG. 5 according to an example of the present application.

FIG. 6 shows a packing density $D_{p1}$ and hydraulic pressure $P_1$ in the central (inner) region 203 of layer 202 and a packing density $D_{p2}$ and hydraulic pressure $P_2$ in the peripheral (outer) region 204 of layer 202 in the sorbent configuration of FIG. 5. The outer edge 213 of peripheral region 204 is contiguous with an inner face 225 of a sidewall 222 of the cartridge housing. $D_{p1}$ is less than (<) $D_{p2}$, and $P_1$ is less than $P_2$, in sufficient amount that fluid flows through the central region 203 of the layer 202 at a similar or substantially similar rate (e.g., within 15% or within 10%, or within 5%) as through the peripheral region 204 during use of the cartridge. $P_2$ can represent a pressure that is present through all or essentially all (e.g., at least 99% by volume) of the packed bed of particles in peripheral region 204 which accommodates fluid flow completely through the layer. $P_1$ can represent a pressure that is present through all or essentially all (e.g., at least 99% by volume) of the packed bed of particles in central region 203 which also accommodates fluid flow completely through the central region 203 of layer 202. The peripheral region 204 has an inner edge 226 that is adjacent and contiguous with an outer edge 217 of the central region 203 that encircles it. In the arrangement of FIG. 6, the inner edge 226 of the peripheral region 204 completely surrounds the central region 203. FIG. 6 shows the peripheral and central regions (204, 203) arranged as concentric circles. Other shapes of the cartridge can dictate different shapes of these regions. For example, a cartridge with a square (or rectangular) cross-sectional shape which has sorbent bed layers loaded therein with complementary geometry can have peripheral and central regions of differential flow created therein that comprise a square-shaped central region inset within an outer square-shaped ribbon of material at the periphery of the layer (not shown).

The packing density $D_{p1}$ of the central region 203 of the layer 202 can be less than the packing density $D_{p2}$ of the peripheral region 204 by at least 1%, 2%, 3%, 4%, 5%, 7.5%, 10%, 15%, 20%, 25%, 30%, 35%, 40% or more, or from 1% to 40%, 2% to 35%, 3% to 30%, 4% to 25%, or 5% to 20%, or any other ranges defined by any two different ones of these values, or other values. The packing density can be determined as a ratio of the mass of the solid particles/total volume occupied by the packed material (particles and interstitial voids). The packing density can be expressed in units of grams/cm$^3$ or other appropriate units. Hydraulic pressure $P_1$ in the central region (203) of the packed particle layer (e.g., 202) can be less than hydraulic pressure $P_2$ of the peripheral region (204) of the same layer by at least 1%, 2%, 3%, 4%, 5%, 7.5%, 10%, 15%, 20%, 25%, 30%, 35%, 40% or more, or from 1% to 40%, 2% to 35%, 3% to 30%, 4% to 25%, or 5% to 20%, or any other ranges defined by any two different ones of these values, or other values. The hydraulic pressure can be expressed in units of millitorrs, pounds per square inch, pascals, or other appropriate units. The hydraulic pressures can be measured at the fluid emergent (top) surface of the particle bed layer. The measurement of the hydraulic pressures of sorbent layers can be done in a manner known in the industry, such as using local sensors, or pressure gauges at the inlet of the sorbent cartridge of the present application. The void fraction of the central region 203 of the layer 202 can be greater than the void fraction of the peripheral region 204 by at least 1%, 2%, 3%, 4%, 5%, 7.5%, 10%, 15%, 20%, 25%, 30%, 35%, 40% or more, or from 1% to 40%, 2% to 35%, 3% to 30%, 4% to 25%, or 5% to 20%, or any other combinations of these values or others. The void fraction refers to the ratio of total inter-particle unoccupied space to the total volume of the bed of particles in a layer. The packing densities $D_{p1}$ and $D_{p2}$ of the different regions 203 and 204, respectively, in the layer 202 can be arranged, for example, wherein $P_2$ is 20 pressure units and $P_1$ is 18 pressure units, wherein $P_1$ is 10% less than $P_2$ (i.e., (20–18/20)×100), for a given set of operational conditions of the cartridge. These indicated values for the hydraulic pressures, packing density differentials and void fractions are not limited to the zirconium phosphate layer exemplified herein, and can apply to other packed bed layers used in sorbent cartridges. The layer 202 can be any layer used in a sorbent cartridge, such as, but not limited to, zirconium phosphate, urease containing layer, zirconium oxide, carbon, and the like.

Figure 7:
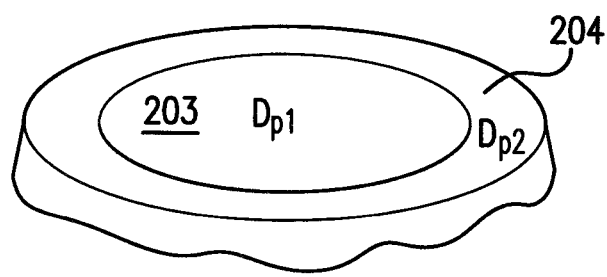
FIG. 7 is a perspective partial view of the sorbent cartridge of FIG. 6 according to an example of the present application.

FIG. 7 shows the central region 203 encircled by the ring-shaped peripheral region 204 from another perspective, wherein the indicated lower packing density $D_{p1}$ is provided in the central region 203 and the higher packing density $D_{p2}$.

Though the sorbent cartridge in FIG. 5 is shown with a tapered shaped sidewall, which has a diameter that smoothly tapers inward towards the outlet end, the indicated concepts described herein also can be applied to cartridges that have other shapes, such as cylindrical, rectangular (e.g., square), hexagonal, or other shapes. The shape can be straight-edged, tapered, stepped, or other shapes. Any geometric shape can generally be used.

Figure 8:
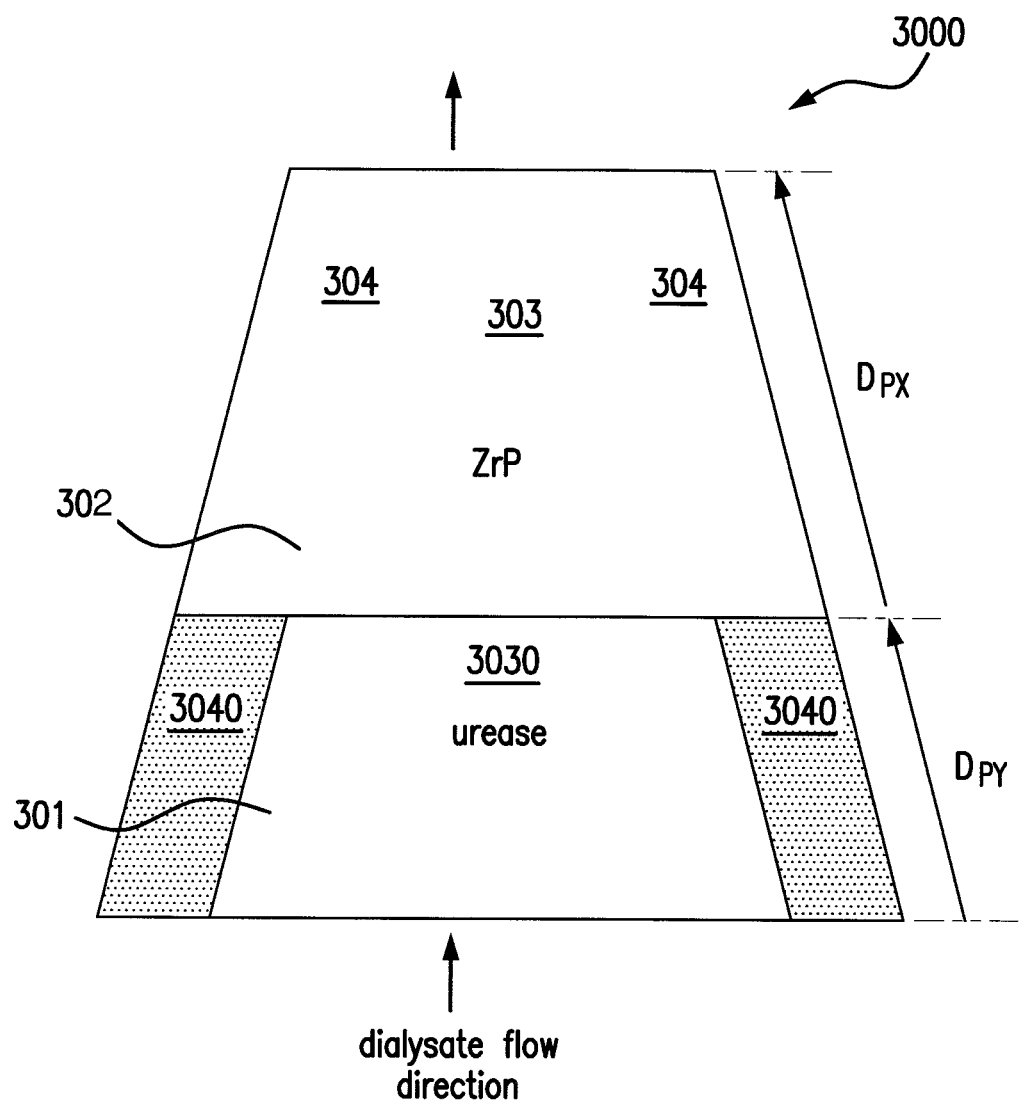
FIG. 8 is an exploded view of materials in one example of a sorbent cartridge which has a packing density differential provided individually in multiple layers thereof according to an example of the present application.

FIG. 8 shows materials in another example of a sorbent cartridge identified as component 3000, which has a packing density differential provided individually in each of a zirconium phosphate layer (layer 1) and a urease layer (layer 2) (but it is to be understood, that layer 1 and layer 2 can be other materials). The layer 302 is provided with a packing density differential $D_{PX}$ and the layer 301 is separately provided with a packing density differential $D_{PY}$. The packing density differential $D_{PX}$ for layer 302 can be provided using any one or more of the concepts described for providing the packing density differential of the layer 202 of the example shown in FIG. 5. Peripheral region 304 of layer 302 can be provided with greater packing density than the central region 303 of the same layer. The packing density differential $D_{PY}$ for layer 301 also can be provided using any one or more of the concepts described for providing the packing density differential of the layer 202 of the example shown in FIGS. 5-7. Peripheral region 3040 of layer 301 can be provided with greater packing density than the central region 3030 of the same layer.

In some examples, one or more layers of a cartridge can have a packing density differential that changes step-wise, gradually, or incrementally in some fashion through the thickness (Y axis) of the layer. In this option, the peripheral region and/or central region can have this option. When the peripheral region has this option, the packing density increases from the bottom of the layer thickness to the top of that layer. When the central region has this option the packing density decreases from the bottom of the layer thickness to the top of the layer. The differential or change in packing density can change every 1%, every 5%, every 10%, every 25%, every 50% of the vertical thickness. The degree of packing density change from the very bottom of layer to the very top of layer can be anywhere from 5% to 200%, such as 10%, 15%, 20%, 25%, 50%, 75%, 100% and the like. This packing density differential for one layer can also apply to more than one layer, with each layer having its own packing density differential. Also, or in the alternative, this packing differential, instead of applying to one layer can apply to two or more layers or all layers, with one example shown in FIG. 9.

As a further option, in addition to providing the indicated packing density differentials on the individual layers, the peripheral region 3040 of the layer 3030 can be provided with a larger value of packing density than the peripheral region 304 of the layer 303. That is, wherein hydraulic pressure in the sorbent bed layers tends to continuously increase from inlet to outlet in the sorbent cartridge, such as for a tapered shaped cartridge or other shapes thereof, the use of a tighter packing density in peripheral regions of layers located relatively closer to the cartridge inlet than another overlying layer or layers can be tolerated and used. In such a configuration, the central region 303 of the layer 302 and the central region 3030 of the layer 301, and any other layers included in the sorbent cartridge, can have similar packing densities with respect to each other, or may differ from each other. Preferably, a packing differential is provided radially and vertically throughout all the layers in the cartridge to ensure uniform flow distribution through all the layers in the cartridge.

Figure 9:
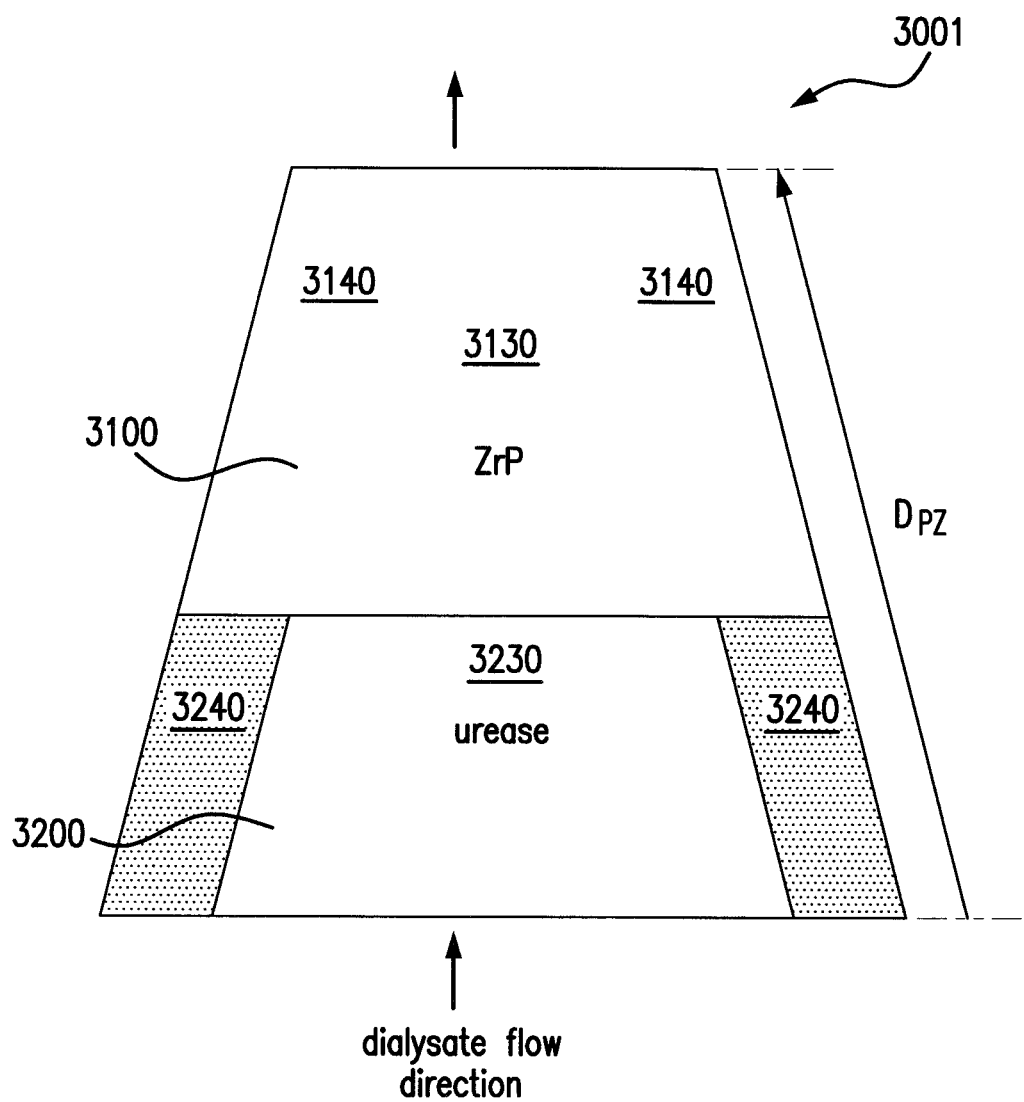
FIG. 9 is an exploded view of materials in one example of a sorbent cartridge which has an overall packing density differential provided over multiple layers thereof according to an example of the present application.

FIG. 9 shows materials in another example of a sorbent cartridge identified as component 3001, which has an overall packing density differential provided over multiple layers comprised of a zirconium phosphate layer and a urease layer. The layer 3100 and the layer 3200 are provided with a packing density differential $D_{PZ}$. The zirconium phosphate layer has a peripheral region 3140 having the packing density differential $D_{PZ}$ with respect to a central region 3130 thereof, and the layer 3200 has a peripheral region 3240 having the packing density differential $D_{PZ}$ with respect to a central region 3230 thereof. The packing density differential $D_{PZ}$ for layer 3100 and the layer 3200 can be provided using any one or more of the concepts described for providing the packing density differential of the layer 202 of the example shown in FIGS. 5-7.

Referring to related FIGS. 10, 11, 12, and 13, FIG. 10 shows materials in an example of a sorbent cartridge, identified as component 400, which have a packing density differential provided in multiple particle bed layers 401, 402, and 403 thereof according to any preceding example such as shown in FIGS. 5-9 or other embodiments of the present application. As shown in FIGS. 10-13, upper layer 403 has a central region 4030 and peripheral region 4031; middle layer 402 has a central region 4020 and peripheral region 4021; and lower layer 401 has a central region 4010 and peripheral region 4011. FIGS. 11, 12, and 13 show the relative sizes of the outer diameters (OD's) of the regions 4031, 4021, and 4011, of higher packing density, as compared to central regions 4030, 4020, and 4010 of lower packing density in corresponding layers 403, 402 and 401, respectively. In this embodiment, the OD of the higher packing density region can be greater in an upper layer as compared to the OD of a lower layer thereto in the cartridge. As an example, the OD of upper layer 403 of the cartridge 400 can be 10, whereas the OD of the middle layer 402 can be 7 and the OD of the lower layer 401 can be 5. The OD's of the layers in the sorbent cartridge can be arranged to increase from the lower inlet end of the cartridge towards to upper outlet end thereof stepwise, incrementally, or layer-by-layer, or with other arrangements.

Figure 14:
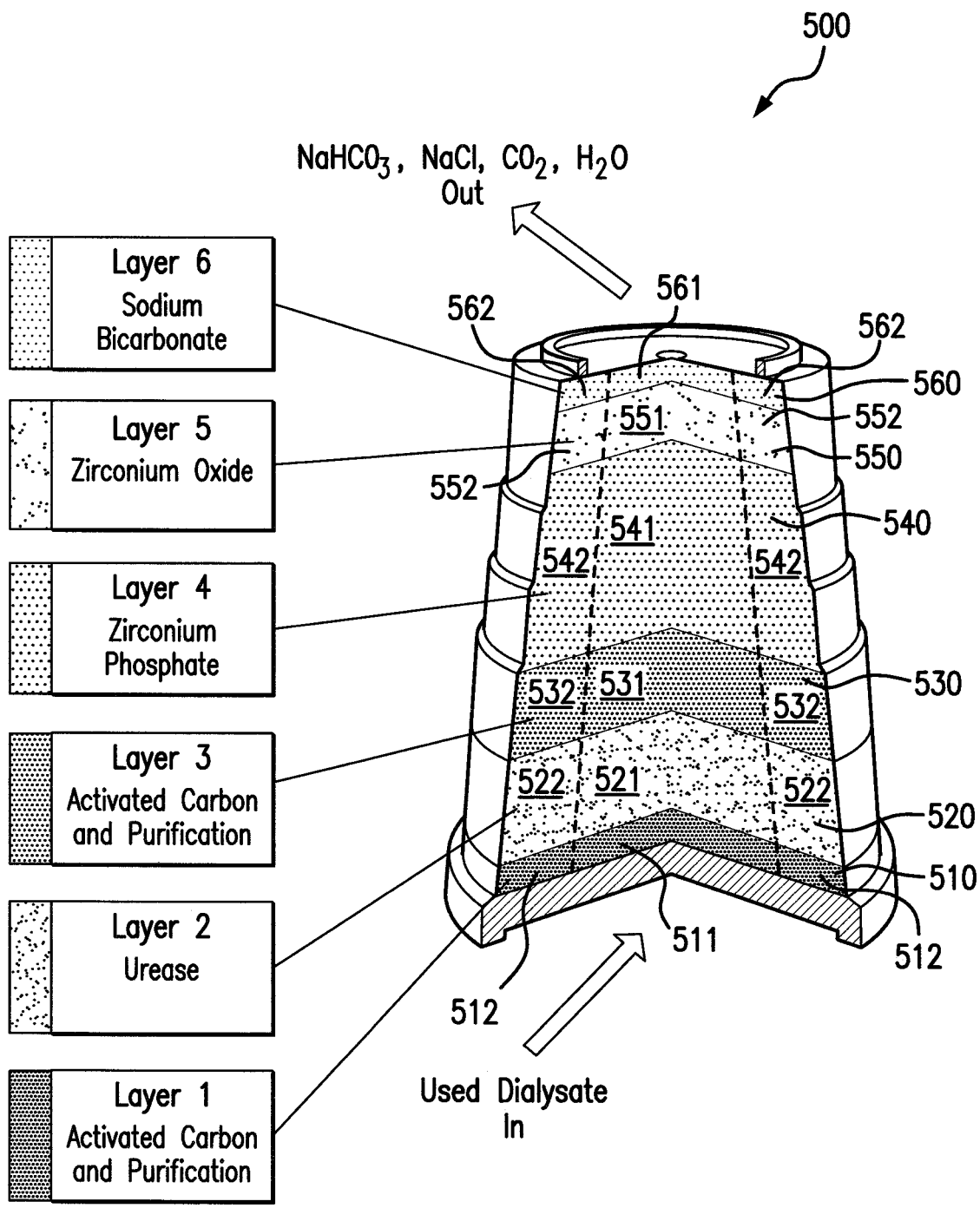
FIG. 14 is an exploded view of materials in one example of a sorbent cartridge which has a packing density differential provided individually or overall in multiple layers thereof according to an example of the present application.

FIG. 14 is an exploded view of materials in one example of a sorbent cartridge, identified as cartridge 500, which has a packing density differential provided individually or overall in multiple layers thereof according to an example of the present application. Cartridge 500 includes an activated carbon layer 510, urease layer 520, activated carbon layer 530, zirconium phosphate layer 540, zirconium oxide layer 550, and sodium bicarbonate layer 560. These layers each form a distinct stratum of the overall particle bed. Additional, different, or less layers can be included in the sorbent bed in the cartridge. The packing density differential can be provided such as shown in any of the indicated examples of FIGS. 5-13 or other examples herein. For example, the packing density can be provided individually layer-by-layer, such as done in the example of FIG. 8, or as an overall value applicable to all the layers, such as done in the example of FIG. 9. As shown in FIG. 14, the activated carbon layer 510 has a central region 511 and peripheral region 512, the urease layer 520 has a central region 521 and peripheral region 522, the activated carbon layer 530 has a central region 531 and peripheral region 532, the zirconium phosphate layer 540 has a central region 541 and peripheral region 542, the zirconium oxide layer 550 has a central region 551 and peripheral region 552, and the sodium bicarbonate layer 560 has a central region 561 and peripheral region 562. Each of the activated carbon layer 510, urease layer 520, activated carbon layer 530, zirconium phosphate layer 540, zirconium oxide layer 550, and sodium bicarbonate layer 560, can be provided with a central region that has a different packing density of particles thereof as compared to a peripheral region thereof. The individual layer or overall layer packing density differential(s) can be provided using any one or more of the concepts described for providing a packing density differential such as described with respect to the examples shown in FIGS. 5-10.

The packing density differential concept described herein is not limited to the examples and kinds of cartridge layers and schemes of layers thereof shown in examples herein, and can be applied to other layers and schemes of sorbent cartridge layers, or other filter devices comprising different kinds of particle layers therein.

The sorbent cartridge(s) described here, in addition to incorporating a packing density differential such as described herein, is/are preferably comprised of layers of highly specified and designed materials, and performs the regenerative function by employing three chemical phenomena: (i) adsorption, (ii) catalysis, and (iii) ion exchange. Adsorption describes the immobilization or fixation of mobile species at a solid interface or surface. Catalysis is a process by which the rate of a chemical reaction is increased by the reduction of the reaction activation energy via a component in the reaction whose net rate of consumption is zero. Ion exchange is a process in which particular solid materials adsorb species for which they have a high affinity and in turn release a species for which its affinity is lower.

In accordance with the techniques described herein, and with no limitation on the layer chemistry, in addition to a packing density differential provided in at least one of the packed bed particle layers, a sorbent cartridge can be provided that can include a housing, a first sorbent layer, and a second sorbent layer and optionally one or more other layers. The housing can define a cartridge interior, the cartridge interior having a volume and configured to hold at least two layers of sorbent material. The housing can include a first end having a first port configured to permit entry of a fluid into the cartridge interior, and a second end distal to the first end and having a second port configured to permit exit of the fluid from the cartridge interior. One will appreciate that the techniques described herein need not be dependent on a particular housing or housing configuration, and that the housing is provided as a conventional way to hold and contain various sorbent layers, as well as effluent passing through the layers. The first sorbent layer can be situated in the cartridge interior. The first sorbent layer can have a first geometry and contain a first sorbent material. The second sorbent layer can be situated in the cartridge interior. The second sorbent layer can have a second geometry and can contain a second sorbent material. The first and second sorbent materials can have equivalent chemical compositions. The first geometry can differ from the second geometry in at least one dimension, or the first sorbent material can differ from the second sorbent material in at least one physical characteristic, or both.

The first and second geometries can differ from one another in one or more desired aspects. For example, the first geometry can differ from the second geometry with respect to size, shape, or both. The first sorbent layer can differ from the second sorbent layer in average height, average width, average length, or a combination thereof. The sorbent cartridge can have a central axis about which the first and second sorbent layers are centered, the first sorbent layer and the second sorbent layer can be cylindrical, or tapered in shape. The first geometry can differ from the second geometry with respect to average height, average radius, or both. The first sorbent layer and the second sorbent layer can differ in volume, weight, and/or density.

The first sorbent layer and the second sorbent layer can differ in surface area. This surface area difference can be achieved by any desired technique and/or configuration. For example, the volume of the first or second sorbent layer can be greater than the other. Alternatively, or in addition, the size and/or shape of particles can differ between the first and second sorbent layers. The difference in particle size can be a difference in average particle size, whether, mean, median, or mode. Accordingly, the first and second sorbent materials can include particles and average particle size of the first sorbent material differs from average particle size of the second sorbent material. The first and second sorbent materials can include particles and at least one of the first and second sorbent materials can include a particle size not present in the other layer. The first and second sorbent materials can contain one or more particle sizes in common, but still different in average particle size. The first and second sorbent materials can include particles and at least one of the first and second sorbent materials can include a particle shape not present in the other layer. The first and second sorbent materials can contain one or more particle shapes in common, but still different with respect to one or more other particle shapes.

The first sorbent layer and the second sorbent layer can differ in sorbent capacity for at least one species targeted for absorption, adsorption, or both. This difference in sorbent capacity can be accomplished by any desired technique and/or configuration. The difference can be independent of chemistry and can instead be a result of one or more differences in volume, density, particle size, and/or particle shape. The first sorbent layer can have a greater sorbent capacity for at least one species targeted for absorption, adsorption, or both, compared to a sorbent capacity of the second sorbent layer for the at least one species, or vice versa.

The first and second sorbent layers can be positioned with respect to one another in any desired manner. For example, the first sorbent layer can be adjacent to the second sorbent layer. The first and second sorbent layer can be separated from one another by one or more additional layers. The first sorbent layer can be proximal to the first end and the second sorbent layer can be proximal to the second end, or vice versa. The first sorbent layer can at least partially surround the second sorbent layer, or vice versa. That is, a given stratum, cross-sectional volume, of the sorbent cartridge can contain one or more layers. Such layers can have chemical compositions, and the first geometry can differ from the second geometry in at least one dimension, the first sorbent material can differ from the second sorbent material in at least one physical characteristic, or both. For example, the sorbent cartridge can have at least one layer defined by a cross-sectional area with an inner region and outer region wherein the outer region surrounds the inner region, and the layer is defined by a height. The first and second sorbent layers can have the same average height with respect to an axial dimension between the first and second ends, and differ with respect to average width, average length, or both. The first and second sorbent layers can be concentric and positioned about a central axis along the axial dimension, the first sorbent layer having a width defined by a first radius extending from the central axis to the second sorbent layer, and the second sorbent layer having a width defined by the difference of the first radius and a second radius greater than the first radius. The sorbent layers can share a common axis, but have geometries that are not circular or even not curvilinear. For example, the geometries can be rectilinear. Circular or other curvilinear geometric layers need not share a common axis, and can be offset from one another with respect to a particular axis of the sorbent cartridge.

With respect to the difference between the first geometry and the second geometry, this difference with respect to size, shape, or both can be a difference of 5% or more, 10% or more, 15% or more, 20% or more, 50% or more, 100% or more, 200% or more, and the like. For instance, the difference can be from about 5% to about 200% with respect to size, shape, or both. Put another way, the comparison of the first sorbent layer and the second sorbent layer with respect to average height, average width, average length or any combination thereof can vary by these percents.

Further, with regard to comparing the first sorbent layer with the second sorbent layer with regard to volume, average density, particle size, (e.g., average particle size), and similar parameters, the difference between the first sorbent layer and the second sorbent layer can vary by these percents as set forth above.

The sorbent cartridge can include at least one additional sorbent layer including a sorbent material having a chemical composition differing from the chemical compositions of the first and second sorbent materials. The at least one additional sorbent layer can be located between the first end and first sorbent layer, between the first and second sorbent layers, or between the second sorbent layer and the second end. The first sorbent layer and the second sorbent layer can be separated from one another by at least one intervening layer including a third sorbent layer having a third geometry and including a third sorbent material, wherein the third sorbent material has a chemical composition non-equivalent to the chemical composition of the first and second sorbent layers. The first sorbent layer and the second sorbent layer can be separated from one another by at least one intervening layer including a third sorbent layer having a third geometry and include a third sorbent material. The first, second, and third sorbent materials can have equivalent chemical compositions, and the third geometry can differ from the first and second geometries, and/or the third sorbent material can differ from the first and second sorbent materials in at least one physical characteristic, and/or the third geometry can differ from either the first geometry or the second geometry as well as differing from either the first sorbent material or the second sorbent material in at least one physical property.

The first and second sorbent materials can have substantially the same or identical chemical compositions. The first and second sorbent materials can have equivalent chemical compositions. For example, the first and second sorbent material can both be cation exchangers, or can both be anion exchangers. The first and second sorbent materials can include at least one cation exchanger. The first and second sorbent materials can include the same cation exchanger. Any desired cation exchanger can be used. For example, the cation exchanger can include zirconium phosphate. The first and second sorbent layers can have the same cation exchange capacity, with respect to one or more types of cations. The first sorbent layer can have a greater cation exchange capacity than the second sorbent layer, or vice versa, with respect to one or more types of cations. The first and second sorbent materials can include at least one anion exchanger. The first and second sorbent materials can include the same anion exchanger. Any desired anion exchanger can be used. For example, the anion exchanger can contain hydrous zirconium oxide. The first and second sorbent layers can have the same anion exchange capacity with respect to one or more types of anion. The first sorbent layer can have a greater anion exchange capacity than the second sorbent layer, or vice versa, with respect to one or more types of anions.

The first and second sorbent materials can include urease, for example, in the form of a Jack Bean paste. The urease in the two different layers can be substantially the same or identical, and can be obtained from such sources as jack beans (for example, *Canavalia ensiformis*), yeasts, and bacteria (for example, *Bacillus pasteurii*). Any urease or combination of ureases can be employed. The urease can differ in specific activity between the two layers. The urease can differ in biological source. The urease can be isolated from a natural source or recombinant.

The first and second sorbent materials can include activated carbon. The activated carbon in the two layers can differ in the degree of activation, and/or both layers can contain non-activated carbon. The type of activated carbon in the two layers can be substantially the same or identical. The layers can share one or more types of activated carbon, but can differ with respect to one or more types of activated carbon. Any type or combination of types of activated carbon can be employed. The carbon can be chemically and/or physically activated. Any desired grade of activated carbon can be used. Examples of activated carbon include powdered activated carbon, granular activated carbon, bead activated carbon, extruded activated carbon, impregnated carbon, polymer-coated carbon, or any combination thereof. Activated carbon can differ with respect to porosity, specific surface area, and/or texture characteristics.

An embodiment described herein includes a sorbent cartridge having an inlet and outlet including at least a first layer and a second layer. The first layer and the second layer can contain particulate material having substantially the same or identical chemical composition. The first layer can be located closer to the inlet than the second layer. The particulate material in the first layer can have at least a greater/higher property then the particulate material in the second layer with respect to average particle size, average surface area, adsorption capacity, or any combination thereof for at least one species.

Non-limiting examples of sorbent cartridges are discussed as follows. Each of these examples can include a housing that surrounds all or a portion of the sorbent layers. The housing can conform to the shape of the sorbent layers in whole or part, or can be independent of the sorbent layer profile. Sorbent layers can be formed using any desired technique. For example, solid molds or hollow frames can be used to form the various strata (horizontal slices) and sorbent layers of a given sorbent cartridge. Sorbent layers of a given stratum can be formed simultaneously or in stages, for example, for successive concentric or nested sorbent layers. Adjacent sorbent layers can have sharp, distinct, blurred, and/or transitioned boundaries. Sorbent layers can contain gradients of sorbent material with respect to density, surface area, composition, and/or any other desired characteristic or combination of characteristics. The shape, size, order, and/or number of the strata and/or layers can vary as desired. Sorbent layers and/or strata can include any shapes or combination of shapes, curvilinear and/or rectilinear, for example, cones, cylinders, conical frustums, polygonal (regular and/or irregular) frustums, cylindrical prisms, conical prisms, polygonal (regular and/or irregular) prisms, and the like. The sides of a sorbent cartridge can be continuous or discontinuous, smooth or stepped, or a combination thereof; a description of one is understood to be representative of the other. Descriptions of square embodiments are also representative of rhombic, rectangular, regular polygonal, and irregular polygonal embodiments, and the like. Any two or more sorbent layers can have equivalent chemical compositions, but differ in respect to geometry and/or physical characteristic. While strata generally refer to horizontal slices, other orientations are also encompassed by the techniques described herein.

As an option, the present invention includes the packing density differential for at least one layer in the absences of housing or sidewalls. For example, it is possible to prepare a layer or multiple layer arrangement and insert this arrangement into housing afterwards. The layer arrangement can be provided in a way that it can be inserted into a cartridge or housing or other holding structure at any time or right before using. The layer arrangement can be structurally kept in place by temporary molds (e.g., paper, plastic, and the like). Thus, the present invention further relates to a sorbent bed comprising at least first and second layers, wherein at least one of the first and second layers comprises a first region, a second region adjacent and surrounding the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density when at least the first and second layers are wet.

The sorbent bed can include a multilayer stack which comprises at least the first and second layers, wherein the multilayer stack is insertable into a sorbent cartridge housing. All of the options, details, discussion above regarding packing density, the layers and the like equally apply here to this aspect of the present invention.

The techniques described herein, in part, can relate to a sorbent cartridge that includes at least dialysate treatment components of carbon, a urease source, zirconium phosphate ("ZP"), zirconium oxide, and (bi)carbonate, wherein at least a portion of the sorbent cartridge incorporates a packing density differential such as described herein, in one layer, several layers, or the whole cartridge.

The layers of materials in a cartridge of the present invention can be situated in the following preferred layer arrangement with these preferred materials from inlet to outlet:

Activated Carbon Layer (inlet)—adsorbs organic species, other lower polarity species such as oxidants and various heavy metal complexes emanating from both the water source and the patient.

Enzyme/Enzyme Retention Layer—the enzyme urease catalyzes the hydrolysis (hydrolytic decomposition) of aqueous urea to form bicarbonate and ammonium. The material used to retain or immobilize the urease can be alumina ($Al_2O_3$).

Activated Carbon Layer—performs same function as first carbon layer; in addition will adsorb organic species emanating from the enzyme source.

Zirconium Phosphate Layer—cation exchange material which adsorbs various cationic species in exchange for hydrogen and sodium ions.

Zirconium Oxide Layer—anion exchange material which adsorb various anionic species in exchange for chloride and hydroxide ions.

Sodium Bicarbonate Layer (outlet)—soluble sodium bicarbonate which dissolves upon priming the cartridge with dialysate thus increasing the concentration of sodium bicarbonate in the dialysate without directly pumping the sodium bicarbonate through the cartridge.

In sorbent dialysis, urea from the patient is transported into the dialysate at the dialyzer. Once in the dialysate, the urea is pumped to the sorbent cartridge where it is hydrolyzed into ammonium and bicarbonate ions. Due to this constant generation of bicarbonate in the dialysate for the duration of the dialysis treatment, the initial concentration of bicarbonate in the dialysate is typically lower in comparison to a normal single-pass dialysis treatment. This initial lower concentration prevents excessive bicarbonate in the dialysate as the treatment progresses, and thus prevents alkalosis. There are two features which have classically made this low initial bicarbonate paradigm safe: (1) a transient low concentration due to the dynamics of the system (not a constant, long duration exposure of low bicarbonate dialysate to a patient); and (2) the low volume ratio of dialysate to patient which inherently prevents the dialysate from driving the patient chemistries.

Compensation for this initial period of low dialysate bicarbonate in sorbent dialysis has classically involved the use of a large concentration of acetate ion donated by the sorbent cartridge which is transported to the patient (gradient driven) and converted to bicarbonate in the liver, thus preventing acidotic symptoms.

However, as an option there is no acetate in the sorbent cartridge. All of the buffer emanating from the cartridge is in the form of bicarbonate. Instead of the sorbent cartridge donating an initial bolus of acetate, the cartridge donates an initial bolus of sodium bicarbonate.

Cartridge designs according to the techniques described herein can provide bicarbonate initially to compensate for the period of lower bicarbonate and allows for a bicarbonate-only total buffer paradigm. Elimination of acetate from the cartridge, and thus the dialysate, a) simplifies the total buffer characterization, and/or b) eliminates potential complications due to acetate intolerance (high initial acetate concentrations coupled with new high flux/high flow rate dialysis), and/or c) eliminates potential alkalosis symptoms due to lack of understanding of the acetate-bicarbonate dynamic.

To reduce acetate, increase or maintain alkalinity, and/or reduce or control soluble Zr within tolerances, a series of layers can be used in the sorbent cartridge which includes a hydrous zirconium oxide layer of hydrous alkaline oxide-chloride that has an alkaline pH, and a (bi)carbonate layer, near or at the effluent outlet end of the cartridge.

A sorbent cartridge described herein can include a hydrous zirconium oxide layer that is hydrous zirconium oxide-chloride (HZO.Cl) having an alkaline pH. The formula for the HZO.Cl can be as in the Background above. To eliminate acetate, increase or maintain alkalinity, and/or reduce or control soluble zirconium within tolerances, HZO—Cl can be provided in the cartridge design. This HZO—Cl layer can be used without sodium zirconium carbonate. Alkaline pH of the HZO—Cl can reduce infused chloride or at least control it to a tolerable level, and can reduce soluble Zr discharge from the cartridge. Increasing alkaline pH can provide greater reductions in infused chloride, soluble Zr, or both. The HZO—Cl layer of alkaline pH can be used in combination with a (bi)carbonate layer that follows the hydrous zirconium oxide layer. The (bi)carbonate layer can comprise sodium carbonate ($Na_2CO_3$), sodium bicarbonate ($NaHCO_3$), or both, at the effluent end of the cartridge.

The hydrous zirconium oxide-chloride can have a pH greater than about 8, or greater than about 9, or about 9.5 to about 10.5, or about 10, or other alkaline values. The pH of the HZO—Cl generally increases with smaller relative proportions of chloride in the HZO—Cl. The chloride content in mg per g of HZO—Cl can be, for example, from about 25 mg/g to about 10 mg/g, or any amount that provides an alkaline pH.

With the cartridge design described herein, one or more further advantages, improvements, and/or properties can be achieved, especially compared to conventional cartridges. For example, it is possible to eliminate acetate content in the sorbent cartridge. In other words, the acetate content in the sorbent cartridge can be 0 wt % or about 0 wt % with respect to any layer and the entire sorbent cartridge. Additionally the sorbent cartridge has the ability to reduce unused material and operate with high dialysate flow rates and/or has the ability to operate with high flux dialyzers and thus have shorter treatment times (e.g., approximately four hours +/−30 minutes). For instance, dialysate flow rates can be from about 300 to about 500 ml/min with reduced unused material as compared to similar sorbent cartridges that lack a packing density differential in one or more particle bed layers thereof. With the use of faster dialysis solution flow rates, this increases the efficiency of diffusion of urea from blood to dialysate. Further still, the techniques described herein have the ability to reduce TOC (total organic carbon) release to levels that are acceptable.

The order and composition of layers for a cartridge design of the present invention prior to be used to regenerate or purify spent dialysis fluid, can be, for example, as follows (e.g., top (exit or outlet) to bottom (entrance-inlet) in the cartridge):

a) one or more layers comprising, consisting essentially of, consisting of, or including sodium bicarbonate (e.g., 20 g to about 30 g), b) one or more layers comprising, consisting essentially of, consisting of, or including hydrous zirconium oxide-hydroxide and/or hydrous zirconium oxide-chloride (e.g., 150 g to about 250 g), c) one or more layers comprising, consisting essentially of, consisting of, or including zirconium phosphate (e.g., 650 g to about 1800 g), for instance, with a sodium loading of from about 50 mg to about 56 mg Na/g zirconium phosphate (the zirconium phosphate can have the formula as set forth in the Background above), d) one or more layers comprising, consisting essentially of, consisting of, or including a carbon layer or pad (e.g., about 50 g to about 500 g carbon), e) optionally one or more layers comprising, consisting essentially of, consisting of, or including alumina or other like material (e.g., about 100 g to about 500 g), f) one or more enzyme containing layers, such as a layer comprising, consisting essentially of, consisting of, or including urease, for example Jack Bean meal with or without alumina blend (e.g., about 100 g to about 400 g, including from about 5 grams to about 50 grams Jack Bean meal), and g) one or more layers comprising, consisting essentially of, consisting of, or including a carbon layer or pad (e.g., about 50 g to about 500 g carbon). These amounts for components a)-g) are provided as an example, and other amounts of these materials may be used.

The order and composition of layers for a cartridge design described herein after being used (or after a few minutes of being used) to regenerate or purify spent dialysis fluid, can be, for example, as follows (e.g., top (exit or outlet) to bottom (entrance-inlet) in the cartridge):

a) one or more layers comprising, consisting essentially of, consisting of, or including hydrous zirconium oxide-hydroxide and/or hydrous zirconium oxide-chloride (e.g., 150 g to about 250 g), b) one or more layers comprising, consisting essentially of, consisting of, or including zirconium phosphate (e.g., 650 g to about 1800 g), for instance, with a sodium loading of from about 50 mg to about 56 mg Na/g zirconium phosphate, c) one or more layers comprising, consisting essentially of, consisting of, or including a carbon layer or pad (e.g., about 50 g to about 500 g carbon), d) optionally one or more layers comprising, consisting essentially of, consisting of, or including alumina or other like material (e.g., about 100 g to about 500 g), e) one or more enzyme containing layers, such as a layer comprising, consisting essentially of, consisting of, or including urease, for example, Jack Bean meal with or without alumina blend (e.g., about 100 g to about 400 g, including from about 5 grams to about 50 grams Jack Bean meal), and f) one or more layers comprising, consisting essentially of, consisting of, or including a carbon layer or pad (about e.g., 50 g to about 500 g carbon). These amounts for components a)-g) are provided as an example, and other amounts of these materials may be used.

As indicated earlier the (bi)carbonate layer, after having spent or used dialysate fluid pass through the cartridge, will dissolve in the dialysate fluid, and disappear or essentially disappear from the cartridge as a layer.

Figure 15:
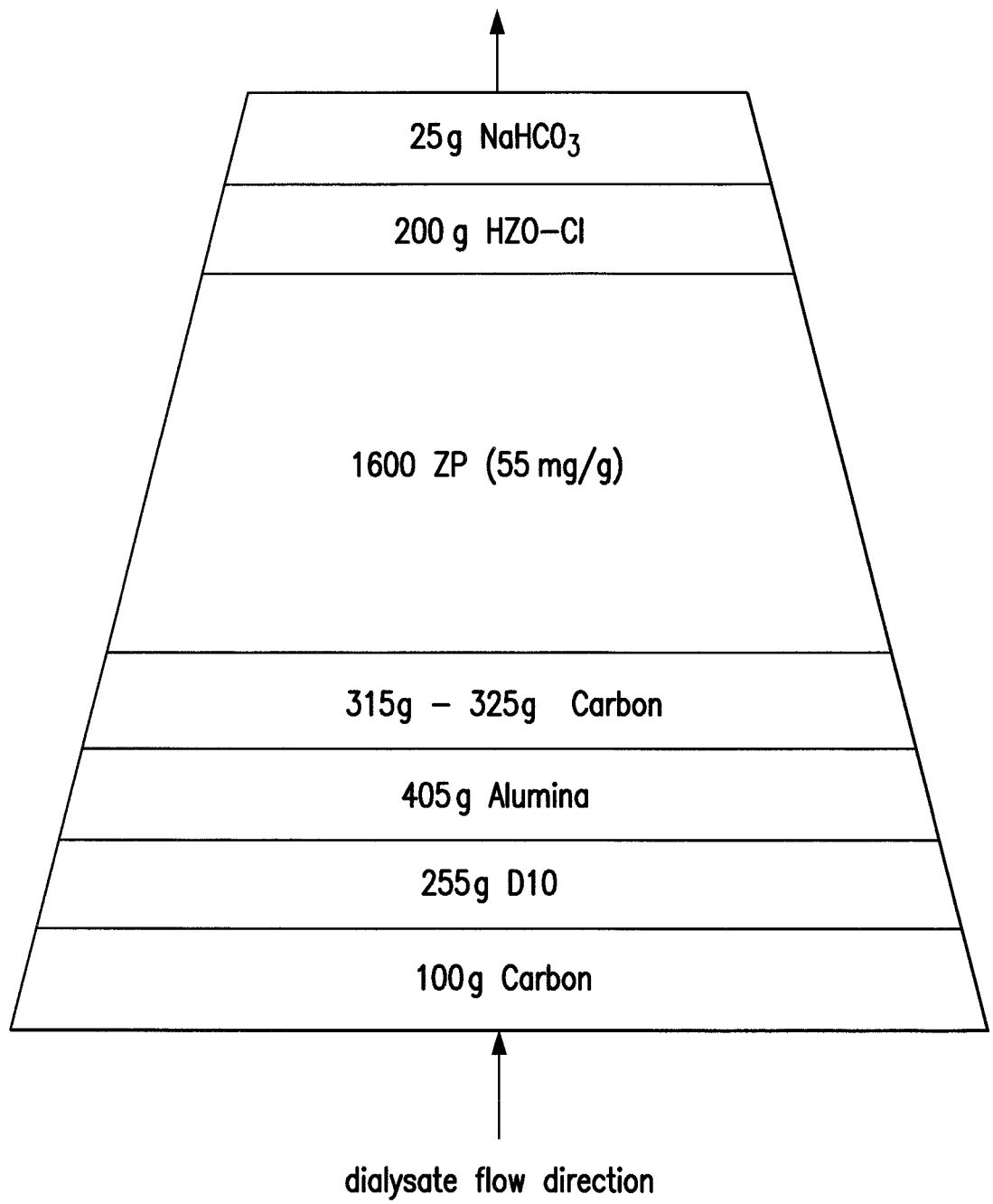
FIG. 15 is an exploded view of materials in a sorbent cartridge according to an example of the present application.

Referring to FIG. 15, in addition to including at least one particle bed layer having packing density differential such as described herein, the sorbent cartridge can comprises a first carbon-containing layer(s), an enzyme-containing layer(s) ("D10") comprising Jack Bean meal that follows the first carbon-containing layer within the sorbent cartridge, an optional alumina layer(s), a second carbon-containing layer(s) that follows the enzyme-containing layer and alumina layer within the sorbent cartridge, a zirconium phosphate-containing layer(s), a hydrous zirconium oxide layer(s) that follows the zirconium phosphate-containing layer comprising hydrous zirconium oxide-chloride that has alkaline pH, and sodium (bi)carbonate layer(s) that follows the hydrous zirconium oxide layer.

In the example of the sorbent cartridge of FIG. 15, sodium (bi)carbonate can be used in an amount of from about 20 g to about 30 g, or from about 22 g to about 28 g, or from about 24 g to about 26 g, or about 25 g, or other amounts. The hydrous zirconium oxide-chloride which has an alkaline pH can be used in an amount of from about 50 g to about 300 g, or from about 75 g to about 200 g, or about 100 g, or other amounts. The zirconium phosphate layer can be used in an amount of from about 650 g to about 1800 g, or from about 800 g to about 1600 g, or from about 900 g to about 1300 g, or other amounts. The zirconium phosphate of this example can have a sodium loading of greater than 55 mg/g Na/g zirconium phosphate, or from about 56 mg to about 58 mg Na/g ZP, or about 57 mg Na/g ZP, or other values. The carbon layer or pad can be used in an amount of from about 50 g to about 500 g carbon or other amounts, the alumina or other like material can be used in an amount of from about 100 g to about 500 g or other amounts, the Jack Bean meal/alumina blend can be used in amounts of from about 100 g to about 400 g, including from about 5 grams to about 50 grams Jack Bean meal or other amounts, and the bottom carbon layer or pad can be used in an amount of from about 50 g to about 500 g carbon or other amounts. Any effective amounts of the above-described materials can be present in the cartridge. These amounts (or any amounts recited herein) can be with respect to a cartridge having the following dimensions: 2 inches-3 inches diameter by 5 inches to 10 inches length, or having the following dimensions: 4 inches-6 inches diameter by 6 inches-12 inches length. However, it is to be understood that these amounts provide weight ratios for each layer with respect to each other layer so as to permit adjustments in any sized cartridge.

A sorbent cartridge can include zirconium phosphate, such as (e.g. as a layer(s)) with increased sodium loading. To eliminate acetate, increase or maintain alkalinity, and/or reduce or control soluble zirconium within tolerances, HZO—Cl can be provided in the cartridge design. This HZO—Cl layer can be used without being combined with the SZC and glass beads. The chloride content of the HZO—Cl can be proportionally reduced sufficient to provide HZO—Cl of an alkaline pH. The hydrous zirconium oxide-chloride can have a pH greater than about 8, or greater than about 9, or about 9.5 to about 10.5, or about 10, or other alkaline values. The pH of the HZO—Cl generally increases with smaller relative proportions of chloride in the HZO—Cl. The chloride content in mg per g of HZO—Cl can be, for example, from about 25 mg/g to about 10 mg/g, or any amount that provides an alkaline pH. Alkalinity may be improved slightly by an increased sodium loading in the zirconium phosphate layer. Increasing alkaline pH can provide greater reductions in infused chloride, soluble Zr, or both. The HZO—Cl layer of alkaline pH can be used in combination with a (bi)carbonate layer that follows the hydrous zirconium oxide layer comprising sodium carbonate ($Na_2CO_3$), sodium bicarbonate ($NaHCO_3$), or both, at the effluent end of the cartridge.

The carbon can be activated carbon particles that are compacted into an activated carbon filter pad. The carbon can be activated carbon particles formed into layer of the particles that can be maintained in position by adjacent layers that adjoin the opposite sides of the carbon layer within the sorbent cartridge. Filter papers, diffusor pads, and separator rings (pads) which may be used, which can have conventional designs and structures for those types of sorbent cartridge components, such as those described in U.S. Patent Application Publication Nos. 2002/0112609 and 2012/0234762, which are incorporated in their entireties by reference herein. The various layers included in the sorbent cartridge usually are permeable to dialysate so that dialysate can continuously flow through the succession of different layers within the cartridge between the inlet and outlet thereof.

Any effective amounts of the above-described materials can be present in the cartridges described herein. For instance, with respect to the total weight of immobilized Jack Bean meal as a source of urease, the immobilized Jack Bean meal can be used in an amount of from about 100 grams to about 400 grams, or from about 150 grams to about 300 grams, or from about 200 grams to about 250 grams, or other amounts. As indicated, the Jack Bean meal can be immobilized, for example, by being blended with filler or the like such as alumina. Jack Bean meal is commercially available, such as from sources such as Sigma-Aldrich. Jack Bean meal can be used in the indicated immobilized form or by itself in amount of from about 5 grams to about 100 grams, or from about 8 grams to about 50 grams, or from about 10 grams to about 30 grams, or other amounts. Generally, the urease source, such as Jack Bean meal, can be present in an amount of from about 22,000 IU or less to about 55,000 IU or more, or from about 28,000 IU to about 42,000 IU. The particle size of the Jack Bean meal can be any effective size such as about 40 mesh or less (or less than about 0.4 mm). The remainder of the immobilized Jack bean meal can be alumina only or combinations of alumina and additional materials. Alumina is commercially available, such as from sources like Alcoa. Alumina can have the formula $Al_2O_3$. A particle size for alumina can be from about 20 microns to about 120 microns, or from about 20 microns to about 40 microns. The carbon in the carbon layers can be activated carbon in any amount and can be present in each carbon layer, for example, in an amount of from about 50 grams to about 500 grams, or from about 100 grams to about 400 grams, or from about 150 grams to about 300 grams, or from about 200 grams to about 250 grams, or from about 225 grams to about 275 grams, or other amounts. As indicated, the carbon can be activated carbon, such as activated granular carbon. The activated carbon is commercially available, such as from sources like Calgon. The activated carbon can have a particle size, for example, of from 0.4 to about 1.2 mm (or 12-50 mesh sieve), or other values. An alumina backup layer optionally can be present in an amount of from about 100 grams to about 500 grams, or from about 200 grams to about 400 grams, or from about 225 grams to about 300 grams, or other values. The particle size for the alumina in a backup layer can be the same as those indicated above for the immobilized Jack Bean meal layer.

As indicated, a sorbent cartridge described herein can be and preferably is acetate free or substantially acetate free. For example, the cartridge can contain less than about 3 wt % total acetate based on total weight of zirconium material and total acetate, or less than about 1 wt % total acetate based on total weight of zirconium material and total acetate, or less than about 0.5 wt % total acetate based on total weight of zirconium material and total acetate, or less than about 0.1 wt % total acetate based on total weight of zirconium material and total acetate, or from 0 to about 3 wt % total acetate based on total weight of zirconium material and total acetate, or from 0 to about 2 wt % total acetate based on total weight of zirconium material and total acetate, or from 0 to about 1 wt % total acetate based on total weight of zirconium material and total acetate, or from 0 to about 0.5 wt % total acetate based on total weight of zirconium material and total acetate, or other ranges within these values. These amounts of zirconium refer to all sources of zirconium in the cartridge, and they also can be applied to any individual layer of zirconium-containing material in the cartridge.

The hydrous zirconium oxide (HZO) component for the cartridges can have the formula $Zr(OH)_4 \cdot nH_2O$. As indicated, the cartridge design described herein can permit this material to be used in acetate-free form or essentially-acetate-free form. Acetate-free hydrous zirconium oxide (HZO) can be prepared, for example, by following the methods such as disclosed in U.S. Patent Application Publication Nos. US 2010/0078387 A1 and US 2006/0140840 A1, which are incorporated in their entirety by reference herein.

The zirconium phosphate can have an adsorption capacity for ammonia, $Ca^{2+}$, $Mg^{2+}$, $K^+$, and toxic heavy metals. As an option, the adsorption capacity of the zirconium phosphate can be approximately from about 20 mg $NH_4$—N/gm ZrP to about 45 mg or more $NH_4$—N/gm ZrP, and can be at least about 30 mg $NH_4$—N/gm ZrP; from about 2 mEq $Ca^{2+}$/gm ZrP to about 7 mEq $Ca^{2+}$/gm ZrP, and can be at least about 3 mEq $Ca^{2+}$/gm ZrP; from about 1 mEq $Mg^{2+}$/gm ZrP to about 5 mEq $Mg^{2+}$/gm ZrP, and can be at least about 2 mEq $Mg^{2+}$/gm ZrP; and from about 3 mEq HM/gm ZrP to about 9 mEq HM/gm ZrP, and can be at least about 6 mEq HM/gm ZrP for heavy metals (HM). Further, the zirconium phosphate can have a $Na^+$ content of from about 1.6 mEq $Na^+$/gm ZrP to about 2.7 mEq $Na^+$/gm ZrP, and can be about 2.2 mEq $Na^+$/gm and a pH of from about 5.5 to about 6. In the cartridge design, separate zirconium phosphate layers can be included which have different sodium content with respect to each other. Other pHs can be used and different $Na^+$ contents can be used with the understanding that reduced sodium loading can be used in the sorbent cartridges described herein. Also, the zirconium phosphate can have a minimum leachable $PO_4^{3-}$ for the material and can be less than about 0.05 mg $PO_4^{3-}$/gm ZrP. Other amounts can be used. In addition, the zirconium phosphate can have an average grain size of from about 30 to about 40 microns and has no residual sulfate or chloride (e.g., less than 0.01%). Other amounts can be used. Furthermore, the zirconium phosphate can satisfy the ANSI/AAMI RD-5-1992 standard on extractable toxic impurities and has a pH when in water of from about 6 to about 7. Further details of the zirconium phosphate and methods of making it, for example, are described in the indicated U.S. Pat. No. 6,627,164 B2, which is incorporated in its entirety by reference herein.

The zirconium phosphate can be used in any amount, subject to practical constraints of the size of the cartridge into which it may be loaded or positioned. As an option, the amount of the zirconium phosphate is a sufficient amount to remove at least partially if not substantially or entirely all of the ammonia present in the spent fluids while providing this performance with reduced sodium loading, such as, compared to the indicated previous cartridge designs.

The cartridge can include with the bicarbonate layer, a second zirconium phosphate with higher sodium loading than a first one, and a hydrous zirconium oxide-hydroxide near the effluent outlet end of the cartridge. The sodium bicarbonate can be used in an amount of from about 20 g to about 30 g, or from about 22 g to about 28 g, or from about 24 g to about 26 g, or other amounts. The second zirconium phosphate layer can be used in an amount of from about 100 g to about 600 g, or from about 400 g to about 600 g, or from about 450 g to about 550 g, or other amounts. The second zirconium phosphate layer can have a sodium loading of from about 64 mg/g ZP to about 70 mg/g ZP, or from about 65 mg/g ZP to about 69 mg/g ZP, or from about 66 mg/g ZP to about 68 mg/g ZP, or other values. The hydrous zirconium oxide-hydroxide can be used in an amount of from about 150 g to about 250 g, or from about 175 g to about 225 g, or from about 190 g to about 200 g, or other amounts. The first zirconium phosphate layer can be used in an amount of from about 650 g to about 1600 g, or from about 800 g to about 1500 g, or from about 900 g to about 1300 g, or other amounts. The first zirconium phosphate layer can have a sodium loading of from about 50 mg/g ZP to about 56 mg/g ZP, or from about 51 mg/g ZP to about 55 mg/g ZP, or from about 52 mg/g ZP to about 54 mg/g ZP, or other values.

Other materials that can also be present in the sorbent cartridge include, but are not limited to, alumina, alumina supported urease, granulated activated carbon, activated alumina, zeolites, diatomaceous earth, direct urea sorbents, and other conventional adsorbent(s), fillers, glass beads, and the like. The materials, amounts, and other optional components and/or dialysis systems described in the following patents and publications can also be used in the present application and are incorporated in their entirety by reference herein and form a part of the present application: U.S. Pat. Nos. 282,578; 3,669,878; 3,669,880; 3,697,410; 3,697,418; 3,703,959; 3,850,835; 3,989,622; 3,989,625; 4,025,608; 4,213,859; 4,256,718; 4,360,507; 4,460,555; 4,484,599; 4,495,129; 4,558,996; 7,033,498 B2, and the following articles, "Guide to Custom Dialysis," Product No. 306100-005, Revision E, pages 1-54, dated September 1993 and "Sorbent Dialysis Primer," Product No. 306100-006, Edition 4, pp. 1-51, dated September 1993 of Cobe Renal Care, Inc.

A single cartridge can be used which combines all of the above-described materials. In another example, a series of cartridges can be used wherein the combination of the above-described materials can be present in one or more cartridges. For instance, urease, alumina, and split carbon layers that sandwich these two layers can be provided in a first cartridge and the remaining layers can be placed in a second cartridge, and so on. Optionally, these various indicated layers in these sequences can be divided over three different cartridges or more. As indicated, all of the materials can be provided in a single cartridge and can be arranged as distinct layers in the single cartridge. As an option, a cartridge layer can be composed of at least about 50% by weight, or at least 75% by weight, or at least about 80% by weight, or at least about 90% by weight, or at least about 95% by weight, or least about 99% by weight, or up to 100% by weight, or from about 50% to about 100% by weight, or from about 75% to about 100% by weight, or from about 90% to about 100% by weight, or from about 95% to about 100% by weight, or from about 99% to about 100% by weight, of only the material or materials indicated for use in that layer.

As an option, in addition to any carbon filter pad that may be used in providing one or both of the indicated carbon layers on each side of the enzyme containing layer, one or more filter pads can be located throughout the sorbent cartridge to ensure that the layer integrity is maintained during operation. The filter pad can be made of any type of material, for instance, standard filter paper or cellulose pads and the like and typically is the diameter or length-width of the cartridge in order to separate completely one layer from another layer. A flow diffuser which uniformly diffuses the used dialysate throughout the entire width or diameter of the sorbent cartridge can be used. The flow diffuser can have a design of radial spreading channels made of plastic or other suitable materials. The flow diffuser is typically located prior to any of the optional filter pads or materials used in the sorbent cartridge and is adjacent to the inlet (or part of the inlet) of the sorbent cartridge. A barrier layer(s) can also be used in the sorbent cartridge. A barrier layer can be located between the immobilized enzyme layer and the alumina layer, if present. An example of a barrier layer includes filter paper and the like.

Various overall shapes of the sorbent cartridge include, but are not limited to, a cylindrical shape, rectangular shape, a pyramidal-cylindrical (stepped) shape as shown, for instance, in FIG. 1 and so on. The shape can be straight-edged or tapered, and so on. Any geometric shape can generally be used. As an option, the PD cartridge has the following dimensions: 2 inches-3 inches diameter by 5 inches to 10 inches length. The HD cartridge can have the following dimensions: 4 inches-6 inches diameter by 6 inches-12 inches long. Other dimensions can be used depending on the needs of the purifying, amount to purify, operating system and the like. Examples of cartridge designs are further shown in U.S. Pat. No. 6,878,283, which is incorporated in its entirety by reference herein. Examples of cartridges are also described in one or more of the patents and/or publications identified herein.

In preparing the Jack Bean meal, the Jack Bean meal can be extracted with a liquid organic solvent, and then the solvent can be evaporated to eliminate organic impurities with the volatiles, and leave intact active urease in the non-evaporated Jack Bean meal residue. The extraction solvent can be, for example, a C1-C4 lower alkyl alcohol such as ethanol, methanol, (iso)propanol, and (iso)butanol, or other liquid organic solvents. Jack Bean meal can be dissolved in ethanol, for example, and then the ethanol can be evaporated to eliminate organic impurities with the volatized fraction and leave an organic, oily residue which contains urease and various higher molecular weight fatty acid derivatives. The evaporation can be promoted by application of heat sufficient to increase volatization without denaturing the urease. The residue can be dried at any temperatures that do not denature the urease, and the resulting dried residue can be used as a purified source of Jack Bean meal and urease remaining therein in a sorbent cartridge, such as an indicated design herein.

As another pretreatment of Jack Bean meal that can be used according to the techniques described herein, urease can be extracted from Jack Bean meal by an extraction process and then the urease can be isolated and lyophilized before incorporation into a sorbent cartridge. Methods for extracting urease from Jack Bean meal can be adapted from known methods in this respect, and the urease extracts can be lyophilized and used in sorbent cartridges. For example, urease may be extracted from Jack Bean meal through steps including solvent extraction, heat treatment, acid precipitation, and lyophilization. The extraction process may be repeated to increase purity of the urease extract product. For extraction of urease, for example, Jack Bean meal may be mixed with acetone and stirred at about room temperature for one or more minutes. The resulting material can be heated to remove cloudy materials, and urease can be precipitated in the remaining supernatant by adjusting the pH of the solution with acid. The acid precipitated urease can be neutralized to a suitable pH, and then lyophilized before use in a sorbent cartridge.

The cartridges as described herein can be used in a variety of separation systems and can be used in the regeneration or purification of dialysates (e.g., HD) or PD solutions. In a less complicated design, spent or used dialysate or PD solutions can simply be passed through one or more cartridges to purify or regenerate the spent fluids. Such a system can be straightforward in setup and can involve merely using a column-type setup wherein the spent fluids are passed from top to bottom wherein gravity permits the spent fluid to go through the cartridge or spent fluid can be passed through the cartridge under pressure which permits the spent fluids to be introduced in any direction. In a more specific system, the system set forth in FIG. 16, and identified by numeral 600, can be adapted to use an indicated, sorbent cartridge as used especially for hemodialysis; that is a system that can be used as a closed system, or alternatively in a single pass dialysis system (not shown). Such a system permits the continuous reusing of the regenerated dialysate in a patient during dialysis treatment. With respect to a single pass system (not shown), in lieu of discarding the used dialysate to a floor drain, as an alternative, the used dialysis can simply be collected in a container which then can be regenerated or purified by passing the spent dialysate through one or more cartridges as described above.

With respect to peritoneal dialysis, there are several options. First, like hemodialysis, the peritoneal dialysis solution that is spent can be directly passed through one or more cartridges to purify or regenerate the used peritoneal dialysis solution in order to remove the waste products. Alternatively, the peritoneal dialysis solution which is used or spent can first be passed through a dialyzer in the same manner as blood during hemodialysis wherein dialysate removes waste products and the like from the peritoneal dialysis solution and then the dialysate can be regenerated or purified by passing the used or spent dialysate through the cartridge. Either system can be used. With a closed PD system the risk of peritonitis can be reduced since the frequent connections which must be made with conventional systems between the catheter in the peritoneal cavity and a succession of dialysis solution containers is avoided in one embodiment.

Figure 16:
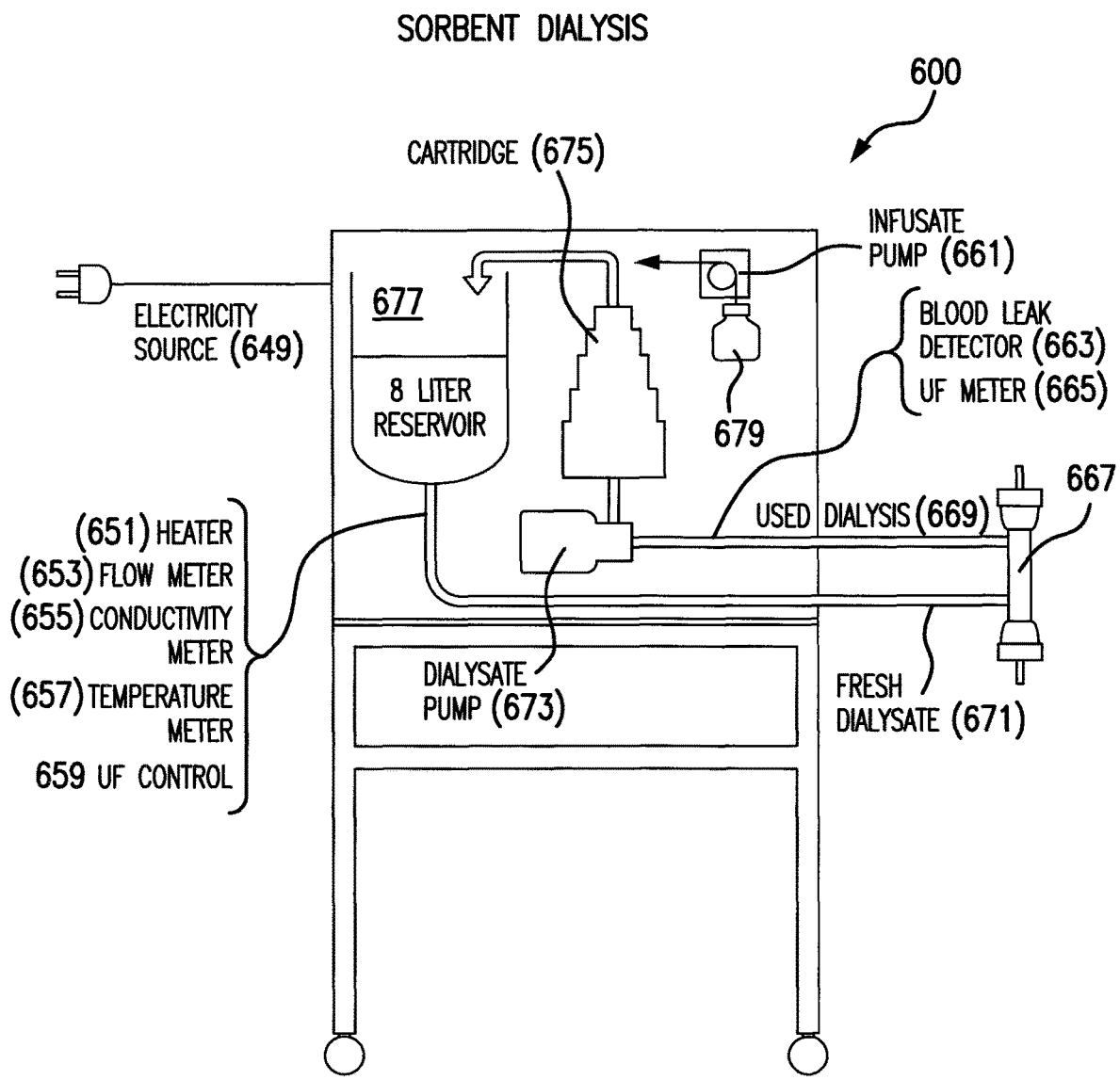
FIG. 16 is a schematic diagram showing a sorbent dialysis system which includes a sorbent cartridge according to an example of the present application.

Referring to FIG. 16, 675 refers to a cartridge, which is a cartridge of the present application. 649 refers to a source of electricity to operate the dialysis system. 651 represents a heater, 653 represents a flow meter, 655 represents a conductivity meter, 657 represents a temperature meter, and 659 represents a UF control. These items are conventional items in a sorbent dialysis system and are known to those skilled in the art and can be used in implementing the techniques described herein. 661 is an infusate pump that is used to pump in fresh concentrate 679 to be mixed with the regenerated dialysate which ultimately enters the reservoir 677 which can be a six liter reservoir. 663 represents a blood leak detector and 665 represents a UF meter which are conventional items in dialysis systems and can be used herein. Component 667 represents a dialyzer. As indicated, a dialyzer is known by those skilled in the art and typically is a system or component that contains a membrane in order to have the waste products pass through the membrane to the dialysate fluid. Similarly, 669 represents used dialysis leaving the dialyzer and 671 represents fresh dialysate entering the dialyzer 667. Component 673 is a pump to pump the used dialysate from the dialyzer into the cartridge 675 which are the cartridges of the present application.

The sorbent cartridges described herein can be made for use in multiple hours of dialysis treatment, such as, for example, for up to about 4 hours of dialysis treatment or for up to about 8 hours of dialysis treatment. For example, the 8 hour cartridges can typically be made for home use and the 4 hour cartridges can typically be made for dialysis treatment in medical treatment or dialysis centers. The cartridges described herein can generally be used with any type of dialysis system as described above. The flows that pass through the cartridge are typically any conventional flows. For instance, flows from about 50 ml/min or less to 500 ml/min or more of dialysate can flow through the cartridge and can be used in the systems described herein. Other flows can be used depending upon the size of the cartridge and the operating system.

The dialysis systems or components thereof described in the above and following patents can be used in the present application and these systems can incorporate the materials and/or cartridges described herein: U.S. Pat. Nos. 7,033,498 B2; 8,663,463; 8,597,505; 8,580,112; 8,500,994; 8,366,921; 8,343,346; 8,475,399; and 8,012,118; and U.S. patent application Ser. No. 14/656,729 filed Mar. 13, 2015. All of these patents and patent applications are incorporated in their entirety by reference herein and form a part of the present application.

There are numerous uses for the materials described herein and especially the cartridges described hereinsuch as the regeneration of dialysis fluids as mentioned above. Furthermore, the cartridges can also be used in any separation process which requires the removal of impurities or waste products from a fluid or other medium that is passable through the materials of the present invention. Also, the techniques described herein may be useful with respect to treating drug overdose patients or other patients which are in need or removing undesirable or dangerous contaminants in a person's blood stream.

Accordingly, the techniques described herein provide useful embodiments that allow the regeneration of dialysate type fluids and other fluids.

The techniques described herein can be used to provide stationary sorbent dialysis systems or portable sorbent dialysis systems. The sorbent dialysis systems can include sorbent hemodialysis, a wearable artificial kidney, sorbent peritoneal dialysis, and other sorbent dialysis systems.

The techniques described herein include the following aspects/embodiments/features in any order and/or in any combination:

1. A sorbent cartridge, comprising:
a continuous sidewall extending between a first end wall and a second end wall, which define a chamber;
at least first and second layers, wherein the at least first and second layers extend across the chamber within the continuous sidewall, wherein at least one of the first and second layers comprises a first region, a second region adjacent the first region and located closer to the continuous sidewall than the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density (e.g., when at least the first and second layers are wet, such as uniformly wet).

2. The sorbent cartridge of any preceding or following embodiment/feature/aspect, wherein the first region is a central region that is surrounded by the second region.

3. The sorbent cartridge of any preceding or following embodiment/feature/aspect, wherein the second region comprises a radially outer peripheral edge extending around the chamber and contiguous with the continuous sidewall and a radially inner peripheral edge which is contiguous with a radially outer side of the first region.

4. The sorbent cartridge of any preceding or following embodiment/feature/aspect, wherein the first packing density in grams per $cm^3$ is at least 5% less than the second packing density in grams per $cm^3$.

5. The sorbent cartridge of any preceding or following embodiment/feature/aspect, wherein the first region has a first void fraction and the second region has a second void fraction, wherein the first void fraction is at least 5% greater than the second void fraction.

6. The sorbent cartridge of any preceding or following embodiment/feature/aspect, wherein the first solid particulate media comprises a first fraction of a supply of solid particles and the second solid particulate media comprises a second fraction of the supply of solid particles, wherein from 90% to 92% by number of solid particles in the second region are finer than solid particles in the first region and from 8% to 10% of the solid particles in the first region are finer than the solid particles in the second region.

7. The sorbent cartridge of any preceding or following embodiment/feature/aspect, wherein the first solid particulate media comprises a first sieve cut of a supply of solid particles wherein the first sieve cut has a first particle size range and the second solid particulate media comprises a second sieve cut of the supply of solid particles wherein the second sieve cut has a second particle size range, wherein the first particle size range comprises at least one particle size that is larger than all the particle sizes of the second particle size range.

8. The sorbent cartridge of any preceding or following embodiment/feature/aspect, wherein the second solid particulate media are arranged as a particle bed comprising multimodal particle packing.

9. The sorbent cartridge of any preceding or following embodiment/feature/aspect, wherein the first solid particulate media are arranged as a particle bed comprising a unimodal particle packing.

10. The sorbent cartridge of any preceding or following embodiment/feature/aspect, wherein the first solid particulate media in the first region has a first crystallinity and the second solid particulate media in the second region has a second crystallinity, wherein the first crystallinity is greater than the second crystallinity which results in greater packing density in the second region than the first region when at least the first and second layers are wet.

11. The sorbent cartridge of any preceding or following embodiment/feature/aspect, wherein a packing density of solid particulate media of the at least one of the two layers increases in a radial direction from a geometric center to an outer peripheral edge of the at least one of the two layers as a monotonic (continuous) increase or a stepped increase.

12. The sorbent cartridge of any preceding or following embodiment/feature/aspect, further comprising an inlet and an outlet, wherein the first and second layers are arranged sequentially with the first layer located closer to the inlet than the second layer, wherein the first layer has a first central region and a first peripheral region that surrounds the first central region, and the second layer has a second central region and a second peripheral region that surrounds the second central region, wherein the first peripheral region of the first layer comprises solid particulate media having a first peripheral region packing density and the second peripheral region of the second layer comprises solid particulate media having a second peripheral region packing density that is less than the first peripheral region packing density.

13. The sorbent cartridge of any preceding or following embodiment/feature/aspect, wherein the at least one of the first and second layers contains particulate material in the first region and the second region having the same or substantially the same chemical composition.

14. The sorbent cartridge of any preceding or following embodiment/feature/aspect, wherein the at least one of the first and second layers contains zirconium phosphate.

15. The sorbent cartridge of any preceding or following embodiment/feature/aspect, wherein both of the first and second layers comprise solid particulate media.

16. The sorbent cartridge of any preceding or following embodiment/feature/aspect, wherein the continuous sidewall having a tapered shape.

17. The present invention relates to a sorbent bed comprising at least first and second layers, wherein at least one of the first and second layers comprises a first region, a second region adjacent and surrounding the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density (e.g., when at least the first and second layers are wet).

18. The sorbent bed of any preceding or following embodiment/feature/aspect, comprising a multilayer stack which comprises at least the first and second layers, wherein the multilayer stack is insertable into a sorbent cartridge housing.

19. The present invention relates to a method to regenerate or purify spent dialysis fluid comprising passing spent dialysis fluid through a sorbent cartridge of any preceding or following embodiment/feature/aspect.

20. The method of any preceding or following embodiment/feature/aspect, wherein unused solid particulate media in the at least one of the first and second layers layer is from 1% to 5% by volume based on total volume of solid particulate media therein.

21. The present invention relates to a dialysis system to regenerate or purify spent dialysis fluid comprising the sorbent cartridge of any preceding or following embodiment/feature/aspect.

22. The present invention relates to a sorbent cartridge, comprising:
   a) a continuous sidewall extending between a first end wall comprising an inlet and a second end wall comprising an outlet, which define a chamber;
   b) an enzyme-comprising layer;
   c) a zirconium phosphate-containing layer that follows the enzyme-comprising layer within the sorbent cartridge, wherein the zirconium phosphate-containing layer comprises a first region, a second region adjacent the first region and located closer to the continuous sidewall than the first region, first solid particulate media in the first region having a first packing density, second solid particulate media in the second region having a second packing density, and a packing density differential between first solid particulate media in the first region and the second solid particulate media in the second region wherein the first packing density is less than the second packing density (e.g., when at least the first and second solid particulate media are wet).

23. The sorbent cartridge of any preceding or following embodiment/feature/aspect, further comprising, from inlet to outlet:
   a) a first carbon-containing layer that precedes the enzyme-comprising layer;
   b) the enzyme-comprising layer, which follows the first carbon-containing layer within the sorbent cartridge;
   c) a second carbon-containing layer that follows the enzyme-comprising layer within the sorbent cartridge;
   d) the zirconium phosphate-containing layer, which follows the second carbon-containing layer within the sorbent cartridge;
   e) a hydrous zirconium oxide layer that follows the zirconium phosphate-containing layer comprising hydrous zirconium oxide-chloride having an alkaline pH; and
   f) a (bi)carbonate layer that follows the hydrous zirconium oxide layer comprising sodium (bi)carbonate.

24. The present invention relates to a method of making a sorbent cartridge, comprising:

a) forming an enzyme-comprising layer that extends across a chamber defined by a continuous sidewall of the sorbent cartridge;
b) forming a solid particulate media-containing layer having a packing density differential that follows the enzyme-comprising layer within the sorbent cartridge, comprising
   i) depositing solid particulate media as a starting layer on the enzyme-comprising layer, wherein the starting layer comprises a first region, and a second region adjacent the first region and located closer to the continuous sidewall than the first region,
   ii) applying a first vibrational or mechanical force to the first region that is less than a second vibrational or mechanical force applied to the second region which results in first solid particulate media in the first region having a first packing density and second solid particulate media in the second region having a second packing density, wherein the first packing density is less than the second packing density.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A sorbent cartridge, comprising:
   a continuous sidewall extending between a first end wall and a second end wall, which define a chamber;
   at least first and second layers, wherein the at least first and second layers extend across the chamber within the continuous sidewall, wherein at least one of the first and second layers comprises a first region, a second region adjacent the first region and located closer to the continuous sidewall than the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density when at least the first and second layers are wet, and wherein the first solid particulate media and the second solid particulate media in at least one of the first and second layers has the same or substantially the same chemical composition.

2. The sorbent cartridge of claim 1, wherein the first region is a central region that is surrounded by the second region.

3. The sorbent cartridge of claim 1, wherein the second region comprises a radially outer peripheral edge extending around the chamber and contiguous with the continuous sidewall and a radially inner peripheral edge which is contiguous with a radially outer side of the first region.

4. The sorbent cartridge of claim 1, wherein the first packing density in grams per $cm^3$ is at least 5% less than the second packing density in grams per $cm^3$.

5. The sorbent cartridge of claim 1, wherein the first region has a first void fraction and the second region has a second void fraction, wherein the first void fraction is at least 5% greater than the second void fraction.

6. The sorbent cartridge of claim 1, wherein the first solid particulate media comprises a first fraction of a supply of solid particles and the second solid particulate media comprises a second fraction of the supply of solid particles, wherein from 90% to 92% by number of solid particles in the second region are finer than solid particles in the first region and from 8% to 10% of the solid particles in the first region are finer than the solid particles in the second region.

7. The sorbent cartridge of claim 1, wherein the first solid particulate media comprises a first sieve cut of a supply of solid particles wherein the first sieve cut has a first particle size range and the second solid particulate media comprises a second sieve cut of the supply of solid particles wherein the second sieve cut has a second particle size range, wherein the first particle size range comprises at least one particle size that is larger than all the particle sizes of the second particle size range.

8. The sorbent cartridge of claim 1, wherein the second solid particulate media are arranged as a particle bed comprising multimodal particle packing.

9. The sorbent cartridge of claim 1, wherein the first solid particulate media are arranged as a particle bed comprising a unimodal particle packing.

10. The sorbent cartridge of claim 1, wherein the first solid particulate media in the first region has a first crystallinity and the second solid particulate media in the second region has a second crystallinity, wherein the first crystallinity is greater than the second crystallinity which results in greater packing density in the second region than the first region when at least the first and second layers are wet.

11. The sorbent cartridge of claim 1, wherein a packing density of solid particulate media of the at least one of the two layers increases in a radial direction from a geometric center to an outer peripheral edge of the at least one of the two layers.

12. The sorbent cartridge of claim 1, further comprising an inlet and an outlet, wherein the first and second layers are arranged sequentially with the first layer located closer to the inlet than the second layer, wherein the first layer has a first central region and a first peripheral region that surrounds the first central region, and the second layer has a second central region and a second peripheral region that surrounds the second central region, wherein the first peripheral region of the first layer comprises solid particulate media having a first peripheral region packing density and the second peripheral region of the second layer comprises solid particulate media having a second peripheral region packing density that is less than the first peripheral region packing density.

13. The sorbent cartridge of claim 1, wherein the at least one of the first and second layers contains zirconium phosphate.

14. The sorbent cartridge of claim 1, wherein both of the first and second layers comprise solid particulate media.

15. The sorbent cartridge of claim 1, wherein the continuous sidewall having a tapered shape.

16. A dialysis system to regenerate or purify spent dialysis fluid comprising the sorbent cartridge of claim 1.

17. A method of making the sorbent cartridge of claim 1, comprising:
applying a first vibrational or mechanical force to the first region that is less than a second vibrational or mechanical force applied to the second region which results in the first average packing density being less than the second average packing density.

18. A sorbent bed comprising at least first and second layers, wherein at least one of the first and second layers comprises a first region, a second region adjacent and surrounding the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density when at least the first and second layers are wet, and wherein the first solid particulate media and the second solid particulate media in at least one of the first and second layers has the same or substantially the same chemical composition.

19. The sorbent bed of claim 18, comprising a multilayer stack which comprises at least the first and second layers, wherein the multilayer stack is insertable into a sorbent cartridge housing.

20. A method to regenerate or purify dialysis fluid comprising passing dialysis fluid through a sorbent cartridge, said sorbent cartridge comprising:
a continuous sidewall extending between a first end wall and a second end wall, which define a chamber;
at least first and second layers, wherein the at least first and second layers extend across the chamber within the continuous sidewall, wherein at least one of the first and second layers comprises a first region, a second region adjacent the first region and located closer to the continuous sidewall than the first region, first solid particulate media in the first region having a first average packing density, second solid particulate media in the second region having a second average packing density, and a packing density differential between the first solid particulate media in the first region and the second solid particulate media in the second region, wherein the first average packing density is less than the second average packing density when at least the first and second layers are wet.

21. The method of claim 20, wherein unused solid particulate media in the at least one of the first and second layers layer is from 1% to 5% by volume based on total volume of solid particulate media therein.

22. A sorbent cartridge, comprising:
a) a continuous sidewall extending between a first end wall comprising an inlet and a second end wall comprising an outlet, which define a chamber;
b) an enzyme-comprising layer;
c) a zirconium phosphate-containing layer that follows the enzyme-comprising layer within the sorbent cartridge, wherein the zirconium phosphate-containing layer comprises a first region, a second region adjacent the first region and located closer to the continuous sidewall than the first region, first solid particulate media in the first region having a first packing density, second solid particulate media in the second region having a second packing density, and a packing density differential between first solid particulate media in the first region and the second solid particulate media in the second region wherein the first packing density is less than the second packing density when at least the first and second solid particulate media are wet.

23. The sorbent cartridge of claim 22, further comprising, from inlet to outlet:
a) a first carbon-containing layer that precedes the enzyme-comprising layer;
b) the enzyme-comprising layer, which follows the first carbon-containing layer within the sorbent cartridge;
c) a second carbon-containing layer that follows the enzyme-comprising layer within the sorbent cartridge;
d) the zirconium phosphate-containing layer, which follows the second carbon-containing layer within the sorbent cartridge;
e) a hydrous zirconium oxide layer that follows the zirconium phosphate-containing layer comprising hydrous zirconium oxide-chloride having an alkaline pH; and
f) a (bi)carbonate layer that follows the hydrous zirconium oxide layer comprising sodium (bi)carbonate.

* * * * *